(12) United States Patent
Ushijima et al.

(10) Patent No.: US 8,273,014 B2
(45) Date of Patent: Sep. 25, 2012

(54) ENDOSCOPIC FLUID CONTROL APPARATUS

(75) Inventors: Takanori Ushijima, Tama (JP);
Toshikazu Yamazaki, Hino (JP)

(73) Assignee: Olympus Medical Systems Corp. (JP)

( * ) Notice: Subject to any disclaimer, the term of this patent is extended or adjusted under 35 U.S.C. 154(b) by 0 days.

(21) Appl. No.: 12/883,294

(22) Filed: Sep. 16, 2010

(65) Prior Publication Data

US 2011/0065998 A1    Mar. 17, 2011

Related U.S. Application Data

(63) Continuation of application No. PCT/JP2009/069505, filed on Nov. 17, 2009.

(30) Foreign Application Priority Data

Mar. 30, 2009   (JP) ................................. 2009-082918

(51) Int. Cl.
*A61B 1/12* (2006.01)
*A61B 1/00* (2006.01)

(52) U.S. Cl. ....................................... 600/159; 600/152

(58) Field of Classification Search .................. 600/158, 600/159, 155, 156, 157, 152
See application file for complete search history.

(56) References Cited

U.S. PATENT DOCUMENTS

| | | | |
|---|---|---|---|
| 4,736,732 A * | 4/1988 | Shimonaka et al. | 600/158 |
| 4,794,913 A * | 1/1989 | Shimonaka et al. | 600/159 |
| 5,257,773 A * | 11/1993 | Yoshimoto et al. | 251/339 |

FOREIGN PATENT DOCUMENTS

| | | |
|---|---|---|
| EP | 1 707 107 | 10/2006 |
| JP | 8-299265 | 11/1996 |
| JP | 9-84756 | 3/1997 |
| JP | 2003-52621 | 2/2003 |
| JP | 2006-524 | 1/2006 |
| JP | 2009-18053 | 1/2009 |
| JP | 2009-45102 | 3/2009 |

OTHER PUBLICATIONS

International Search Report and Written Opinion mailed Dec. 22, 2009 in corresponding PCT International Application No. PCT/JP2009/069505. English translation of International Search Report issued on Dec. 22, 2009 in connection with corresponding PCT application No. PCT/JP2009/069505.
Supplementary European Search Report for co-pending European Application No. EP 09843068 dated Jun. 6, 2011.

\* cited by examiner

*Primary Examiner* — Anhtuan Nguyen
*Assistant Examiner* — Alireza Nia
(74) *Attorney, Agent, or Firm* — Ostrolenk Faber LLP

(57) ABSTRACT

An endoscopic fluid control apparatus includes a cylinder which is attachable to an attachment part attached to an endoscope, and includes a first channel which transfers fluid to an insertion channel of the endoscope, a piston which is set on the cylinder and includes a valve part movable relative to the cylinder between a position where the first channel is opened relative to the insertion channel and a position where the first channel is closed relative to the insertion channel, a connection port part for connecting a fluid tube, and a second channel which transfers the fluid from the connection port part to the insertion channel, an elastic member which holds the piston to be movable relative to the cylinder between the position where the first channel is closed and the position where the first channel is opened, a first engagement part which engages the piston and the elastic member with each other so as not to rotate about an axis of movement of the piston, and a second engagement part which engages the cylinder and the elastic member with each other so as not to rotate about an axis of movement of the cylinder.
The piston includes the valve part, a connection port part, and the second channel.

4 Claims, 24 Drawing Sheets

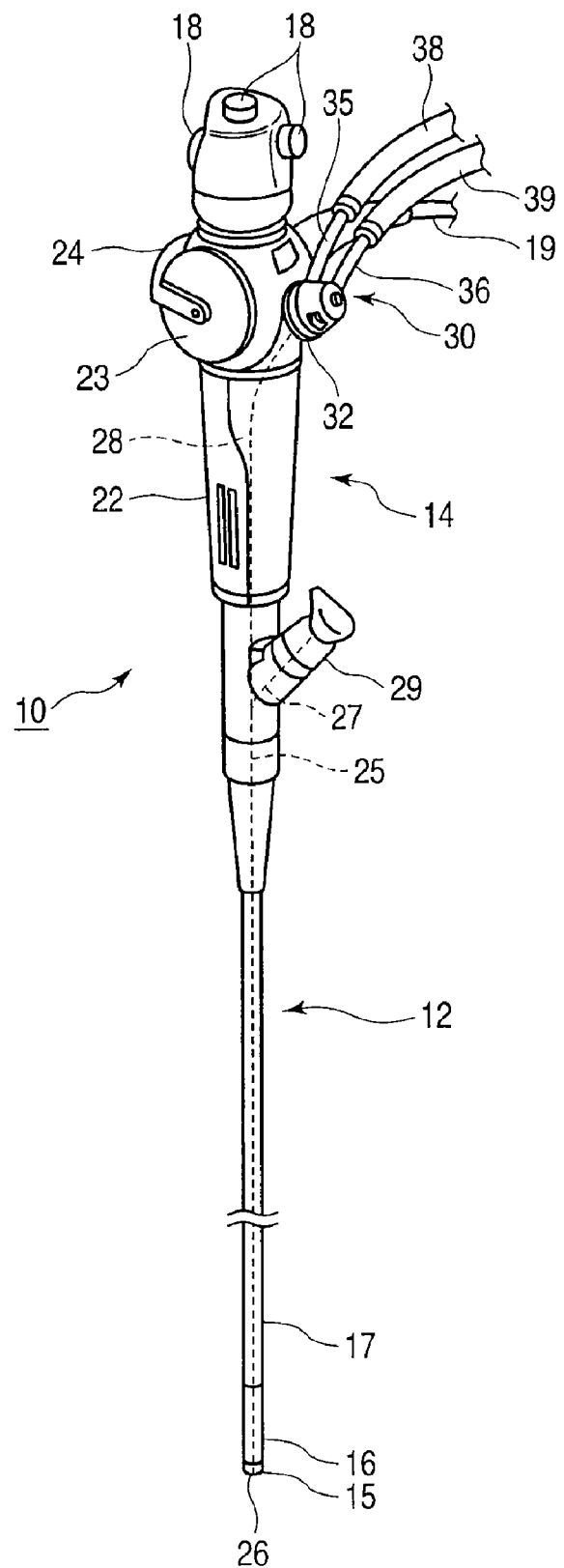
F I G. 1

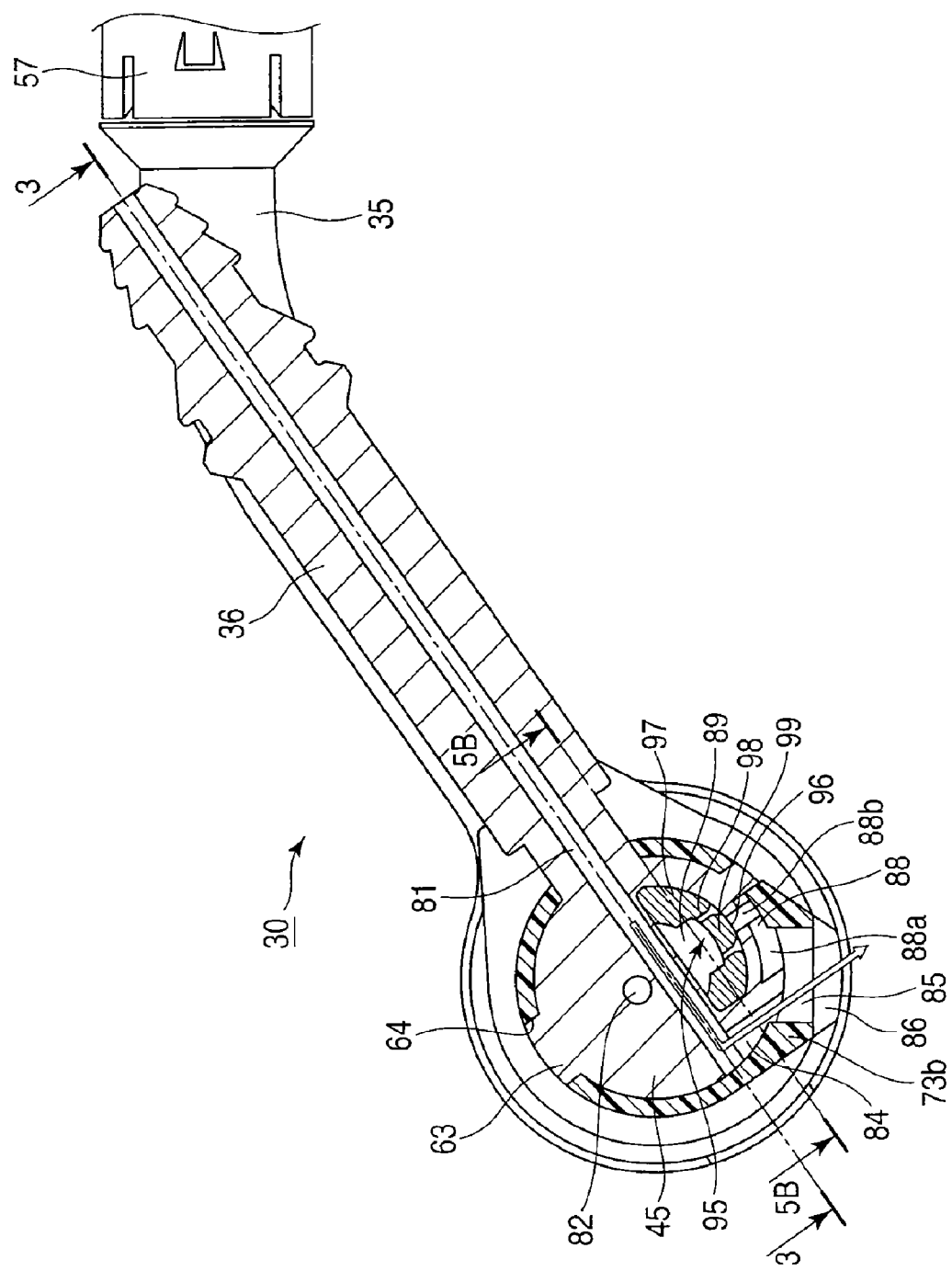
F I G. 5A

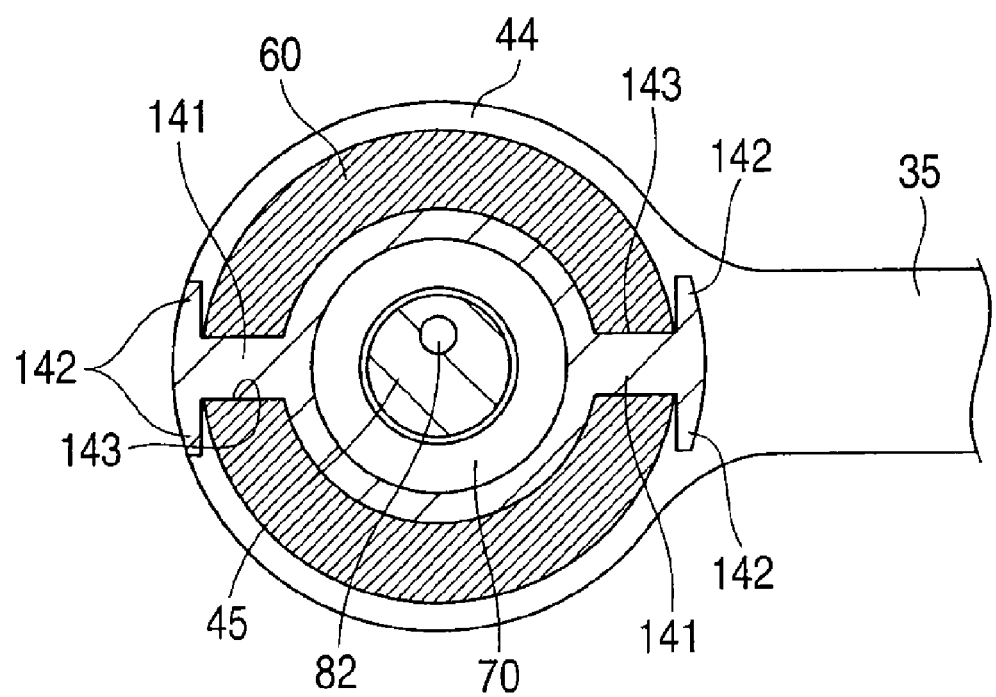
F I G. 7

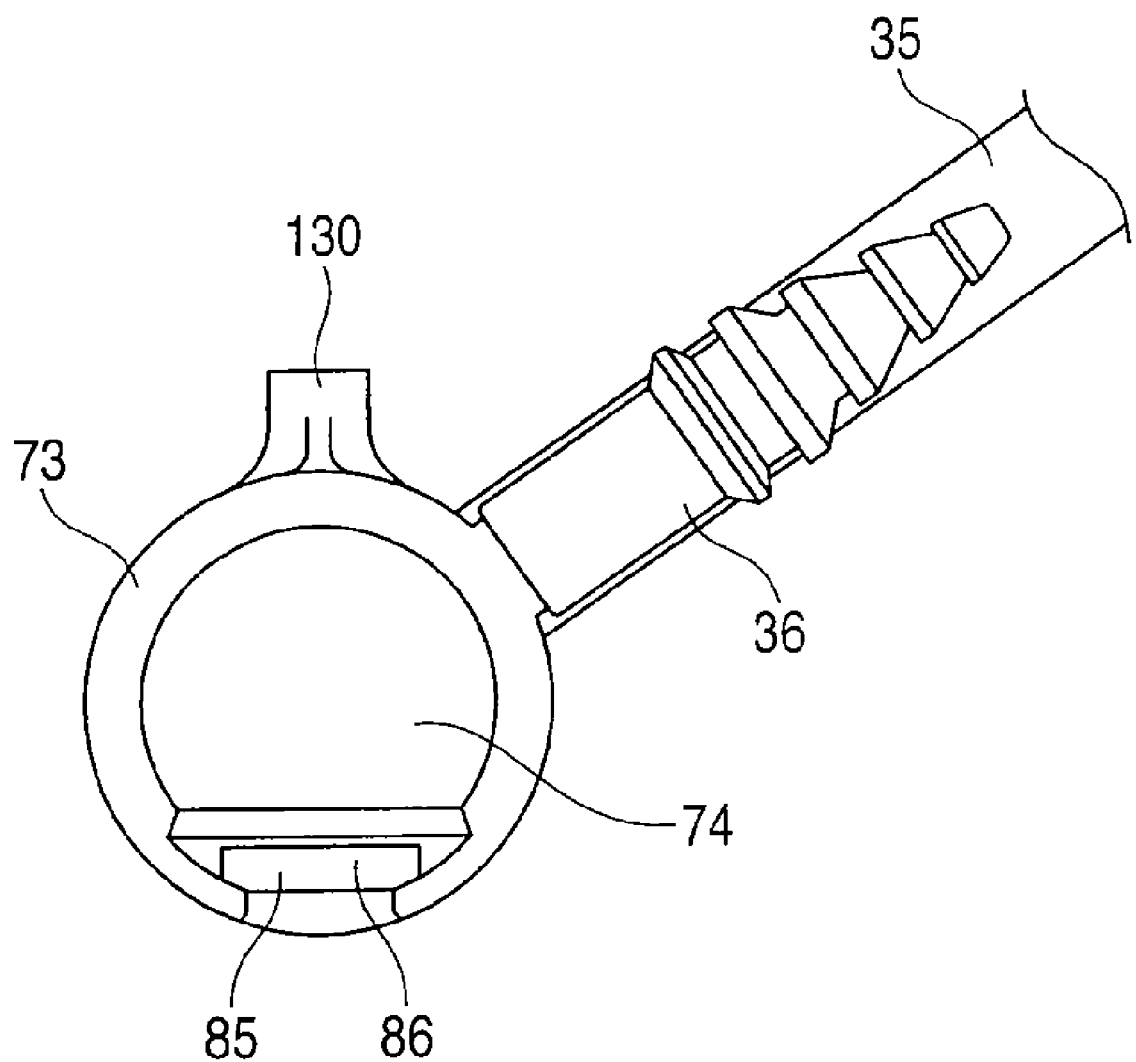
F I G. 10

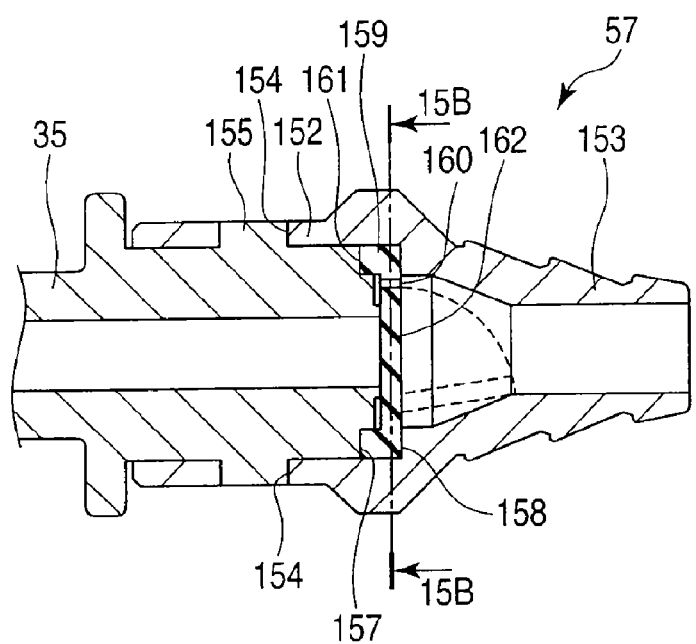
F I G. 15A
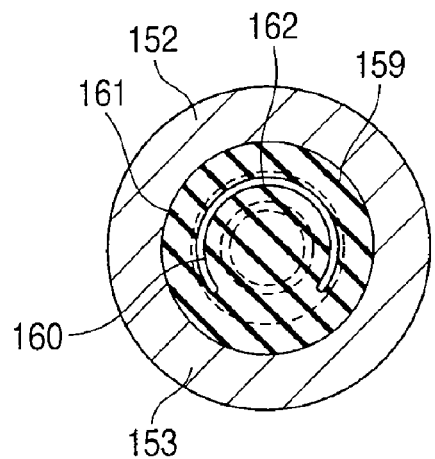
F I G. 15B

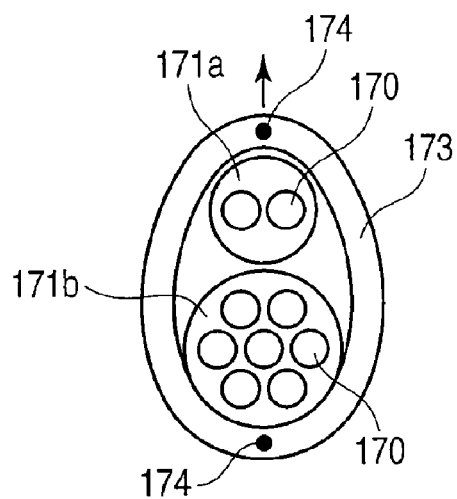
F I G. 19A
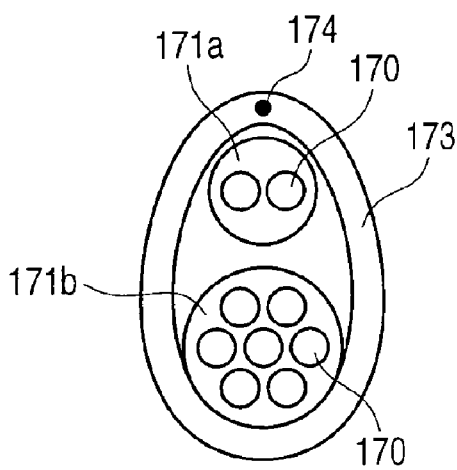
F I G. 19B

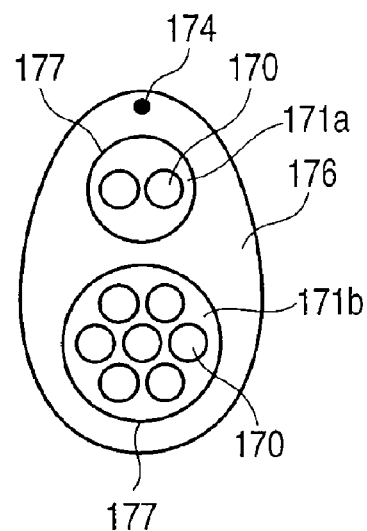
F I G. 19C
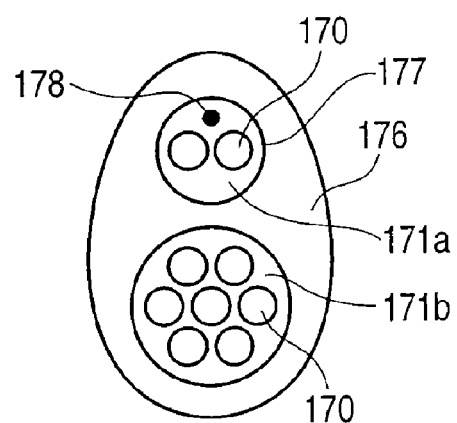
F I G. 19D

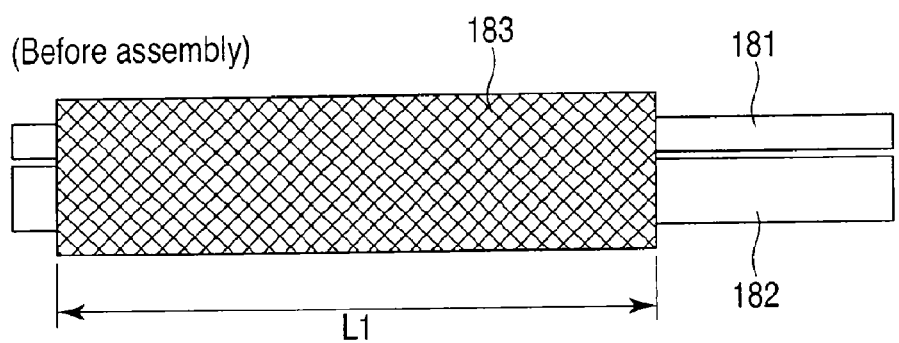
F I G. 20A
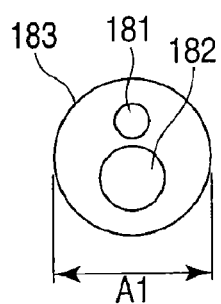
F I G. 20B (During suction)

(During suction)

(During suction)

ENDOSCOPIC FLUID CONTROL APPARATUS

CROSS-REFERENCE TO RELATED APPLICATIONS

This application is based upon and claims the benefit of priority from the prior Japanese Patent Application No. 2009-082918, filed Mar. 30, 2009; and PCT/JP2009/069505, filed Nov. 17, 2009, the entire contents of all of which are incorporated herein by reference.

BACKGROUND OF THE INVENTION

1. Field of the Invention

The present invention relates to an endoscopic fluid control apparatus which controls the flow of fluid in an endoscope.

2. Description of the Related Art

In general, an endoscope comprises an insertion part which is inserted into a body cavity, and a manipulation part connected to a base end of the insertion part. An endoscope also comprises channels through which fluid flows for feeding or suctioning air or water. Movement of fluid is controlled by a fluid control apparatus provided in the manipulation part (see for example, Jpn. Pat. Appln. KOKAI Publication No. 9-84756, Jpn. Pat. Appln. KOKAI Publication No. 2003-52621, and Jpn. Pat. Appln. KOKAI Publication No. 8-299265).

Recently, there has been a proposal for a method in which a single valve device controls both the air feed and suction for channels in an endoscope (Jpn. Pat. Appln. KOKAI Publication No. 2009-18053). This fluid control apparatus is constituted by a cylinder and a piston body. The cylinder is engaged in an attachment tube provided on a manipulation-part body of the endoscope. A protrusion formed on an outer surface of the cylinder engages in an engagement concave formed in an inner surface of the attachment tube. In this manner, the cylinder is detachably attached to the manipulation-part body so as not to easily detach. Between the attachment tube and the cylinder, there is provided a cam mechanism which floats up the cylinder in a direction of falling off from the attachment tube, thereby assisting in the release of the cylinder, as the cylinder rotates.

Further, a metal suction mouthpiece is provided at an upper end of the cylinder which protrudes from the attachment tube. A suction tube is connected to the metal suction mouthpiece. Further, a metal air-feed mouthpiece is provided at a top end of the piston body which protrudes out of the cylinder. An air-feed tube is connected to the metal air-feed mouthpiece.

BRIEF SUMMARY OF THE INVENTION

According to an aspect of embodiments, an endoscopic fluid control apparatus includes: a cylinder which is attachable to an attachment part attached to an endoscope, and includes a first channel which transfers fluid to an insertion channel of the endoscope; a piston which is set on the cylinder and includes a valve part movable relative to the cylinder between a position where the first channel is opened relative to the insertion channel and a position where the first channel is closed relative to the insertion channel, a connection port part for connecting a fluid tube, and a second channel which transfers the fluid from the connection port part to the insertion channel; an elastic member which holds the piston to be movable relative to the cylinder between the position where the first channel is closed and the position where the first channel is opened; a first engagement part which engages the piston and the elastic member with each other so as not to rotate about a axis of movement of the piston; and a second engagement part which engages the cylinder and the elastic member with each other so as not to rotate about an axis of movement of the cylinder.

Advantages of the invention will be set forth in the description which follows, and in part will be obvious from the description, or may be learned by practice of the invention. Advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

FIG. 1 is a perspective view illustrating an endoscope according to an embodiment of the present invention;

FIG. 5A is a cross sectional view illustrating the fluid control apparatus laterally cut along a plane along the center of the metal air-feed mouthpiece (along a line 5A-5A in FIG. 2);

FIG. 7 is a cross sectional view laterally cut along a line 7-7 in FIG. 2;

FIG. 10 is a plan view of fluid control apparatus in FIG. 8;

FIG. 15A is a longitudinal sectional view illustrating a tube connection part of the metal suction mouthpiece of the fluid control apparatus;

FIG. 15B is a cross sectional view cut along a line 15B-15B in FIG. 15A;

FIG. 19A illustrates a layout of signal lines illustrated in FIG. 18;

FIG. 19B illustrates another layout of the signal lines illustrated in FIG. 18;

FIG. 19C illustrates another layout of the signal lines illustrated in FIG. 18;

FIG. 19D illustrates another layout of the signal lines illustrated in FIG. 18;

FIG. 20A illustrates a state before assembling the imaging cables in a blade, and a structure of covering the imaging cables with the blade;

FIG. 20B is a front view of FIG. 20A;

DETAILED DESCRIPTION OF THE INVENTION

Figure 2:
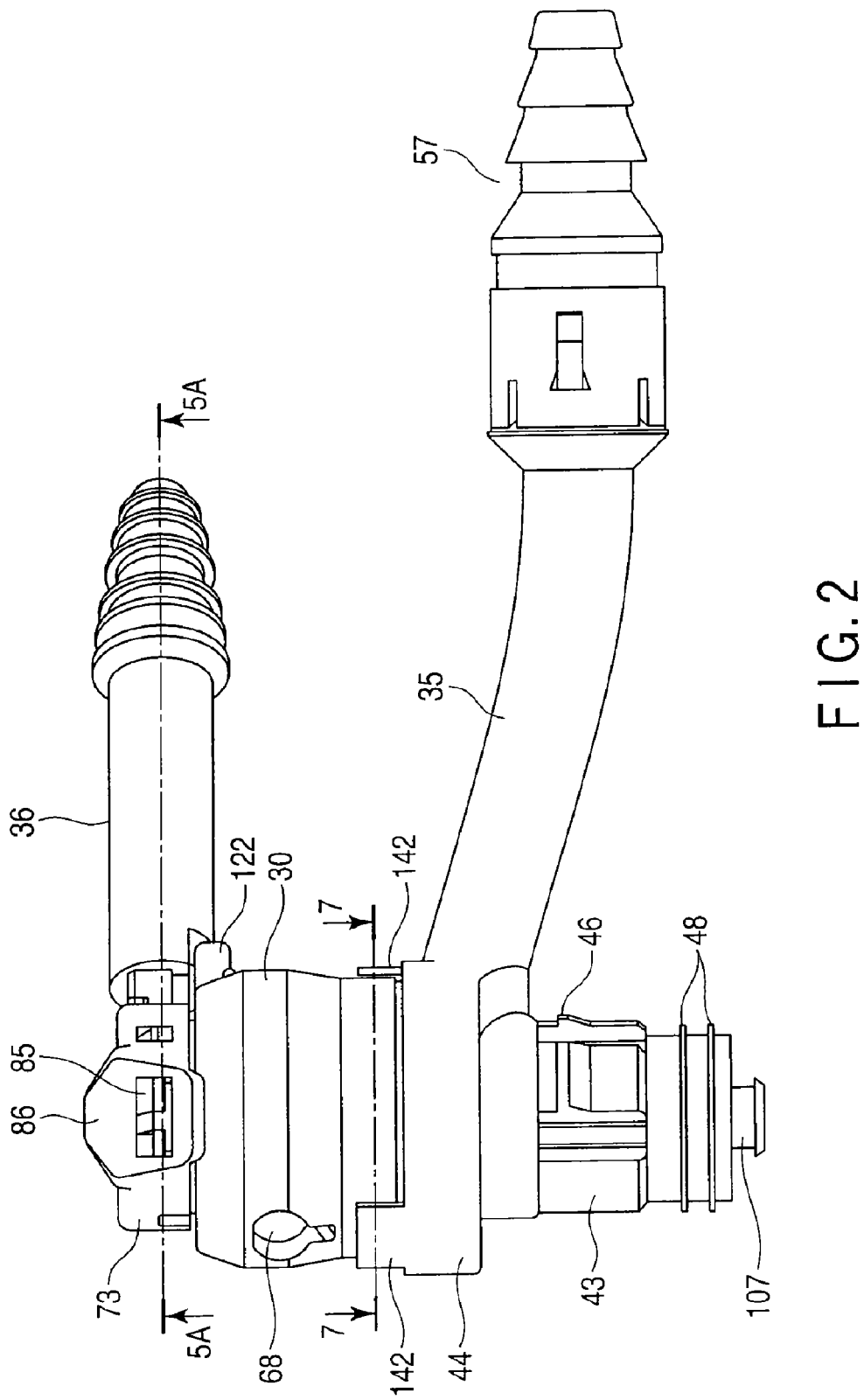
FIG. 2 is a side view of a fluid control apparatus of the endoscope.

Hereinafter, an embodiment of the present invention will be will be described in detail.

FIG. 1 is a perspective view illustrating an endoscope 10 in an endoscopic device according to an embodiment of the invention. This endoscope 10 comprises an elongate endoscope insertion part 12 which is inserted into a body cavity, and an endoscope manipulation part 14 which is connected to a base end of the endoscope insertion part 12. The endoscope insertion part 12 is constituted by connecting a tip end structure 15, a bendable part 16 which is operated to bend, and a flexible tube part 17 which is long and flexible, in this order from a base end side. An unillustrated illumination window and an imaging observation window are provided in the tip end structure 15. In this manner, the endoscope insertion part 12 is inserted into a body cavity, and the inside of the body cavity is then imaged and observed. The endoscope manipulation part 14 comprises an endoscope grip part 22 which is gripped by an operator, and an endoscope manipulation-part body 23 positioned closer to the base end than the endoscope grip part 22. The endoscope manipulation-part body 23 is provided with a bend lever 24 for bending the bendable part 16. Plural operation switches 18 for controlling imaging are provided at a hand-side part of the endoscope manipulation part 14. A universal cord 19 which guides an unillustrated light guide and a signal cable from a side of the endoscopic device is connected to the endoscope manipulation part 14.

In the endoscope manipulation-part body 23, there is provided a bend drive mechanism (unillustrated) which is operated by the bend lever 24. This bend drive mechanism is operated by the bend lever 24, to bend the bendable part 16 by using an unillustrated manipulation member such as a manipulation wire part inserted in the endoscope insertion part 12.

An insertion channel 25 for inserting an instrument such as a treatment instrument is formed from the tip end of the endoscope insertion part 12 to the inside the endoscope manipulation part 14. The insertion channel 25 serves as a channel for both air feed and suction. A tip end of the insertion channel 25 is open in the tip end structure 15, and forms an opening 26 for suction and air feed and for allowing the treatment instrument to protrude. Inside the endoscope manipulation part 14, the insertion channel 25 is branched into a channel 27 in a side of an insertion port for the treatment instrument, and a channel 28 in a side of an endoscopic fluid control apparatus 30 described later. The channel 27 of the treatment instrument is connected to an insertion port 29 for inserting the treatment instrument, etc. The channel 28 in the side of the fluid control apparatus 30 is connected to an attachment part 32. The endoscopic fluid control apparatus 30, described later, is detachably attached to the attachment part 32.

FIG. 2 is a side view of the fluid control apparatus 30. The fluid control apparatus 30 is provided with the metal suction mouthpiece (suction-tube connection port part) 35 and the metal air-feed mouthpiece (air-feed-tube connection port part) 36. As illustrated in FIG. 1, a suction tube 38 is connected to the metal suction mouthpiece 35, and an air-feed tube 39 is connected to the metal air-feed mouthpiece 36. A protruding tip end of the suction tube 38 is detachably connected to a suction device such as an unillustrated suction pump. The suction tube 38 is a suction channel communicating with the insertion channel 25 and channel 28 which constitute one channel. A protruding tip end of the air-feed tube 39 is detachably attached to an air-feed device such as an unillustrated air-feed pump.

Next, the fluid control apparatus 30 will be specifically described. The fluid control apparatus 30 has a structure configured as a single valve device, into which a suction control valve mechanism and an air-feed control valve mechanism are integrally assembled, and the structure is attachable/detachable to/from the endoscope 10.

Figure 3:
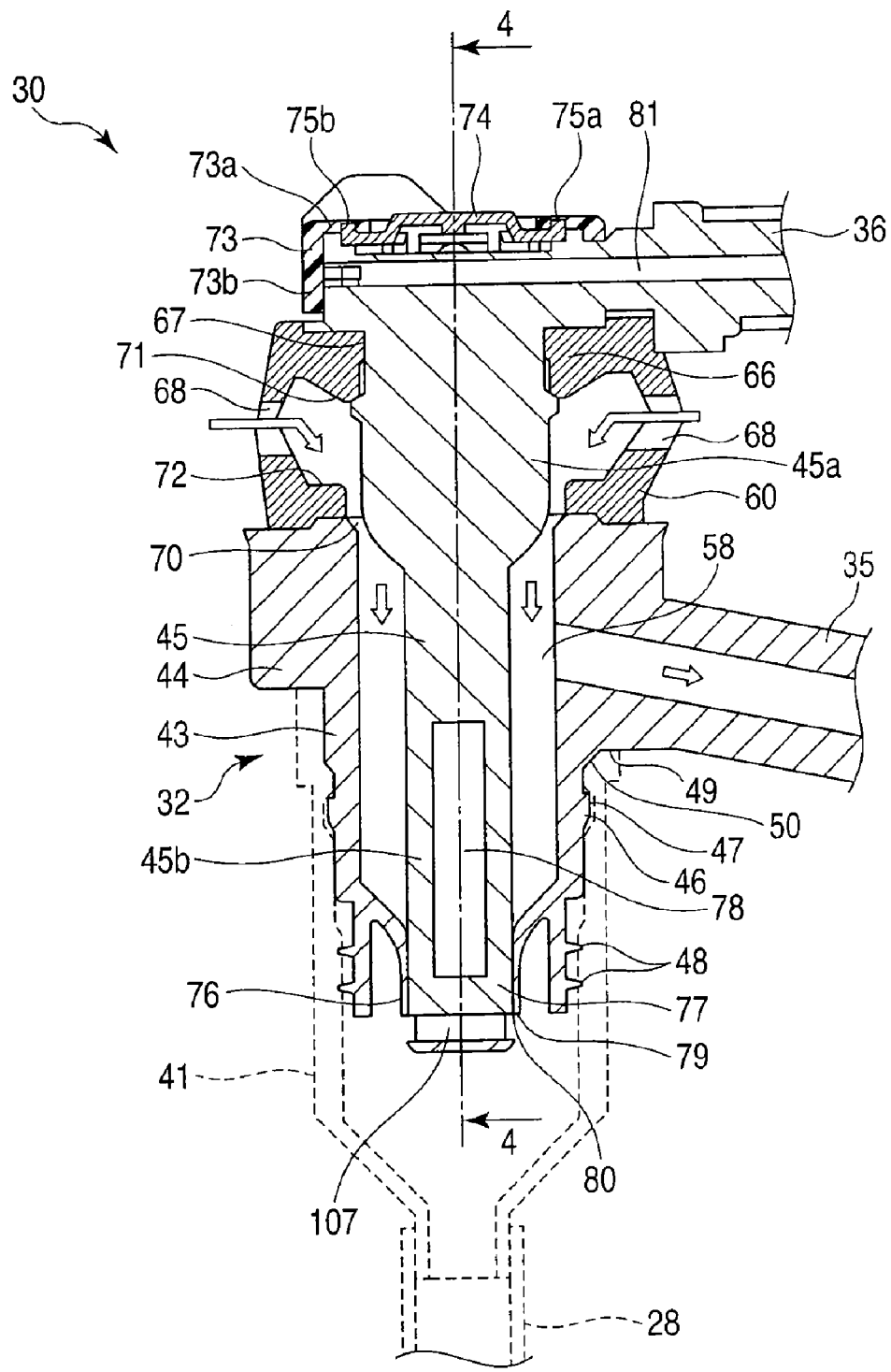
FIG. 3 is a longitudinal sectional view illustrating the fluid control apparatus longitudinally cut along a plane along centers of a suction base metal and a metal air-feed mouthpiece (along a line 3-3 in FIG. 5A)

As illustrated in FIG. 3, the attachment part 32 to which the fluid control apparatus 30 is attached comprises a circular attachment tube 41 provided on the endoscope manipulation-part body 23. The attachment tube 41 is fixed to the endoscope manipulation-part body 23. A top end of the attachment tube 41 faces a side of an outer surface of the endoscope manipulation-part body 23, and opens to the exterior. An inner end (lower end) of the attachment tube 41 is positioned inside the endoscope manipulation-part body 23 and is connected to the channel 28.

As illustrated in FIG. 3, the fluid control apparatus 30 comprises a cylinder 43 having a substantially circular tube shape such as a valve device body, and a piston body 45 provided inside the cylinder 43. The fluid control apparatus 30 controls suction from the insertion channel 25 by pushing in the piston body 45 with a finger. A lower end of the cylinder 43 is detachably engaged into (attached to) the attachment tube 41. The cylinder 43 is attached to the attachment part 32 (attachment tube 41) in a manner such that the top end of the cylinder 43 is exposed to the exterior of the attachment tube 41. Specifically, a flange 44 which is thicker than an inner diameter of the attachment tube 41 is formed on an outer circumference of the cylinder 43. This flange 44 makes contact with an outer end surface of the attachment tube 41, thereby defining an insertion attachment position of the cylinder 43 in relation to the attachment tube 41.

As illustrated in FIG. 3, an inner circumferential wall surface of the attachment tube 41, and an outer circumferential wall surface of the cylinder 43 engaged in the attachment tube 41 are provided with engagement parts which mutually engage with each other. The engagement parts comprise a convex 46 formed on either one of the outer circumferential wall surface of the cylinder 43 and the inner circumferential wall surface of the attachment tube 41, and a concave 47 formed on the other one of the outer circumferential wall surface of the cylinder 43 and the inner circumferential wall surface of the attachment tube 41. As the convex 46 and concave 47 engage with each other, the attachment tube 41 supports (holds) the cylinder 43. The convex 46 and concave 47 are provided so as to extend over a whole circumference of the attachment tube 41 or the cylinder 43 about an axis thereof. A sealing protrusion 48 which seals an inward part of the attachment tube 41 from outside is provided on an outer circumference of the lower end of the cylinder 43. The sealing protrusion 48 is provided to extend over the whole circumference of the cylinder 43 about an axis thereof. Further, a ring-shaped gasket (unillustrated) is attached to an outer circumferential part of the cylinder 43 engaged in the attachment tube 41. In this manner, much tighter sealing is achieved between the engagement parts of the attachment tube 41 and cylinder 43. In this manner, the cylinder 43 is maintained to be air-tight to the attachment tube 41. Further, the cylinder 43 can rotate about its own center axis while maintaining a sealed state. Further, the cylinder 43 is fixedly held by the attachment tube 41, owing to an engagement force and a friction force with respect to the attachment tube 41.

Figure 6:
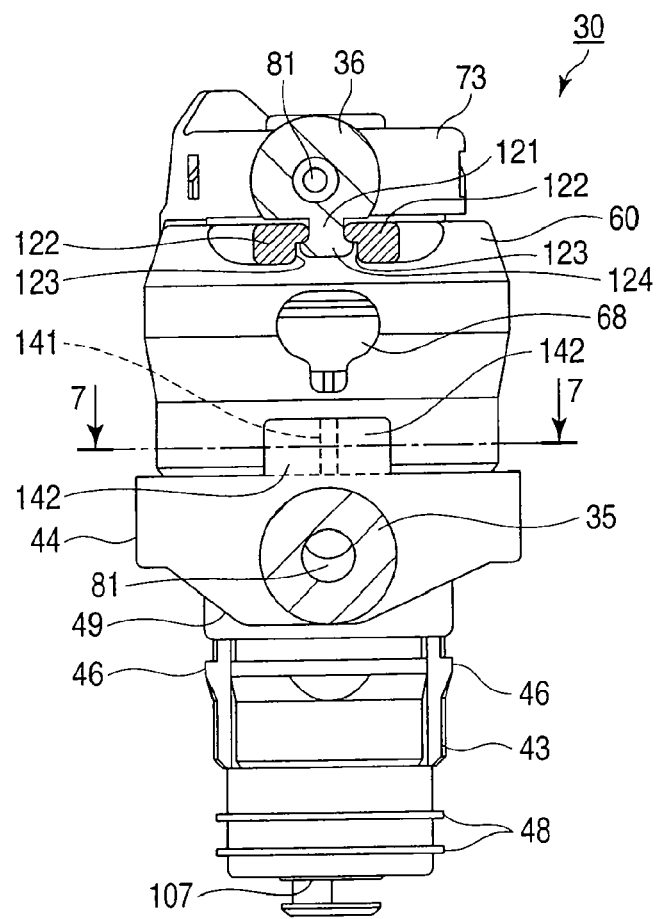
FIG. 6 is a front view of the fluid control apparatus, viewed from a side of the suction base metal and metal air-feed mouthpiece.

As illustrated in FIGS. 3 and 6, a cam part 49 having a convex shape and protruding downward is formed at a part of a lower surface of the flange 44. The part of the lower surface of the flange 44 means, for example, a part positioned below the metal suction mouthpiece 35. As illustrated in FIG. 3, a cam receiving part 50 is formed at an edge of a top end of the attachment tube 41 which is opening. The cam receiving part 50 is an engagement part opposed to the cam part 49, is to be engaged with the cam part 49, and has a concave shape. The cam part 49 and cam receiving part 50 function as a cam mechanism which assists in detaching the cylinder 43 when the cylinder 43 is detached from the attachment tube 41. When the fluid control apparatus 30 is attached to the attachment tube 41, the cylinder 43 is engaged into the attachment tube 41 in a predetermined direction. Then, the cam part 49 engages with the cam receiving part 50, and the cylinder 43 is attached at a predetermined position relative to the attachment tube 41, as illustrated in FIG. 3. When the fluid control apparatus 30 is detached from the attachment tube 41, the cam part 49 takes off (detaches) from the cam receiving part 50 and pulls up the attachment tube 41 from the cylinder 43, as the cylinder 43 rotates about its axis. Accordingly, the cylinder 43 can be easily detached from the attachment tube 41.

As illustrated in FIGS. 2 and 3, the metal suction mouthpiece 35 is formed on the flange 44 in a substantially circular tube shape to be integral with the cylinder 43. The metal suction mouthpiece 35 is protruded toward a side of the cylinder 43. A suction tube connection part 57 for connecting the suction tube 38 is provided at a tip end of the metal suction mouthpiece 35.

Further, as illustrated in FIG. 3, a suction channel 58 as a first channel is formed inside the cylinder 43 and an inner hole of the metal suction mouthpiece 35. That is, the cylinder 43 comprises the first channel (suction channel 58) which transfers fluid to the insertion channel 25.

Figure 4:
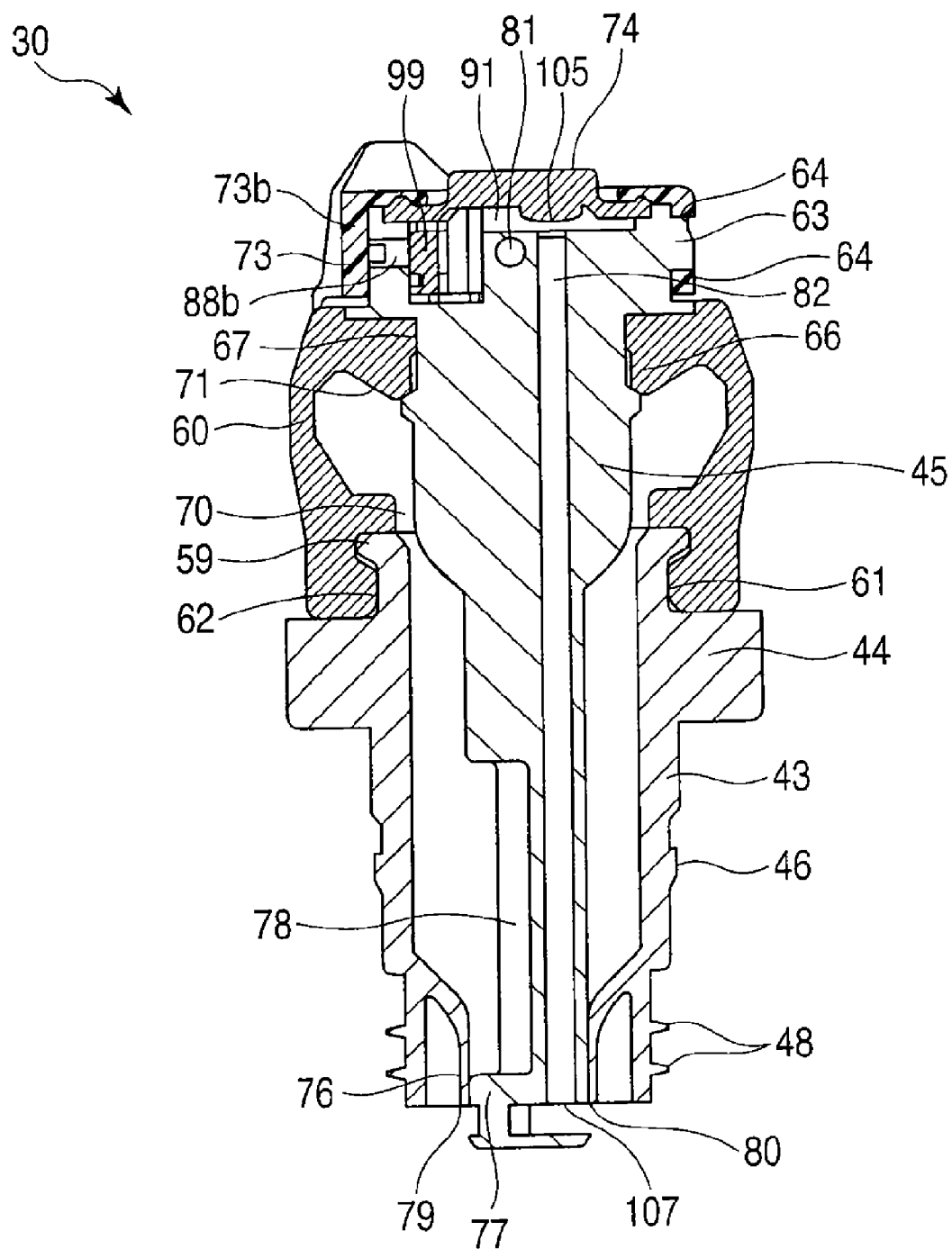
FIG. 4 is a longitudinal sectional view illustrating the fluid control apparatus longitudinally cut along a plane perpendicular to the plane along the centers of the suction base metal and metal air-feed mouthpiece (along a line 4-4 in FIG. 3)

As illustrated in FIG. 4, the top end of the cylinder 43 engages with a lower end of an elastic member 60. Specifically, a circular connection part 59 having a smaller diameter than the flange 44 is formed at the top end of the cylinder 43. A concave 61 extended over the whole circumference of the cylinder 43 about an axis thereof is formed in an outer circumference of the connection part 59. The elastic member 60 is formed of elastic rubber into a substantially cylindrical shape. A convex 62 extended over a whole circumference of the elastic member 60 about an axis thereof is formed on an inner circumferential surface of the lower end of the elastic member 60. Further, the convex 62 is engaged into the concave 61. Therefore, an opening part at the lower end of the elastic member 60 is covered and engaged on the outer circumference of the connection part 59. The elastic member 60 air-tightly connects with the cylinder 43. Further, the lower end of the elastic member 60 engages with the top end of the cylinder 43, with the lower end thereof sealed in tight contact with the cylinder 43. The lower end of the elastic member 60 is also fixedly attached to the cylinder 43, with the lower end sealed in tight contact with the cylinder 43. At this time, the lower end of the elastic member 60 is attached to the top end of the cylinder 43, with the lower end of the elastic member 60 positioned coaxial to the cylinder 43.

As illustrated in FIG. 3, the elastic member 60 is shaped in a substantially cylindrical shape. A center part of the top end of the elastic member 60 is open. The piston body 45 attached to the cylinder 43 is inserted into the elastic member 60 so as to penetrate upward into the elastic member 60. A convex 66 is formed on an inner circumferential surface of the top end of the elastic member 60. The convex 66 is provided so as to protrude inward and extend over the whole circumference of the elastic member 60 about an axis thereof. Further, a concave 67 is formed in an outer circumference of the top end of the piston body 45. The concave 67 is provided so as to extend over the whole circumference of the cylinder 43 about the axis thereof. As the convex 66 is engaged in the concave 67, the top end of the elastic member 60 engages with the top end of the piston body 45, with both top ends sealed in tight contact with each other. The top end of the elastic member 60 is fixedly secured to the piston body 45.

Figure 23A:
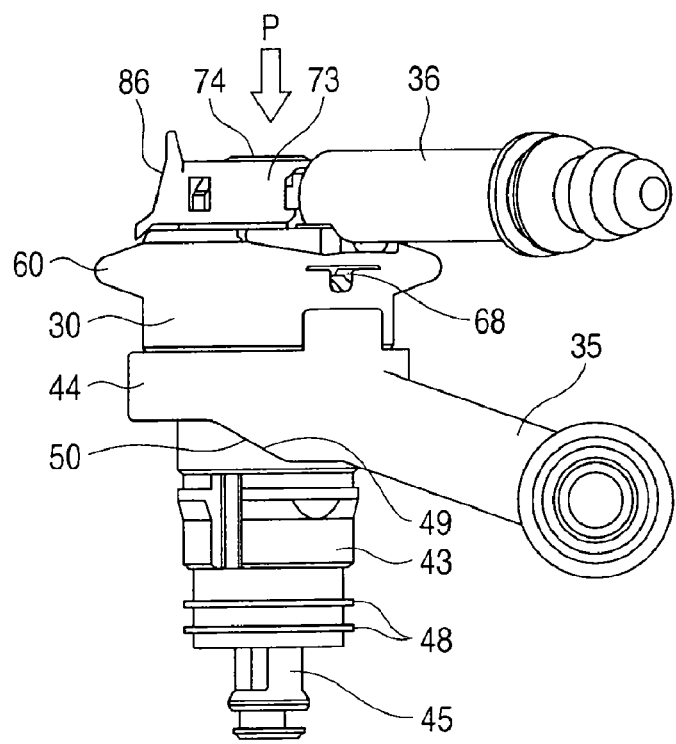
FIG. 23A is a side view of the fluid control apparatus during suction.
Figure 23B:
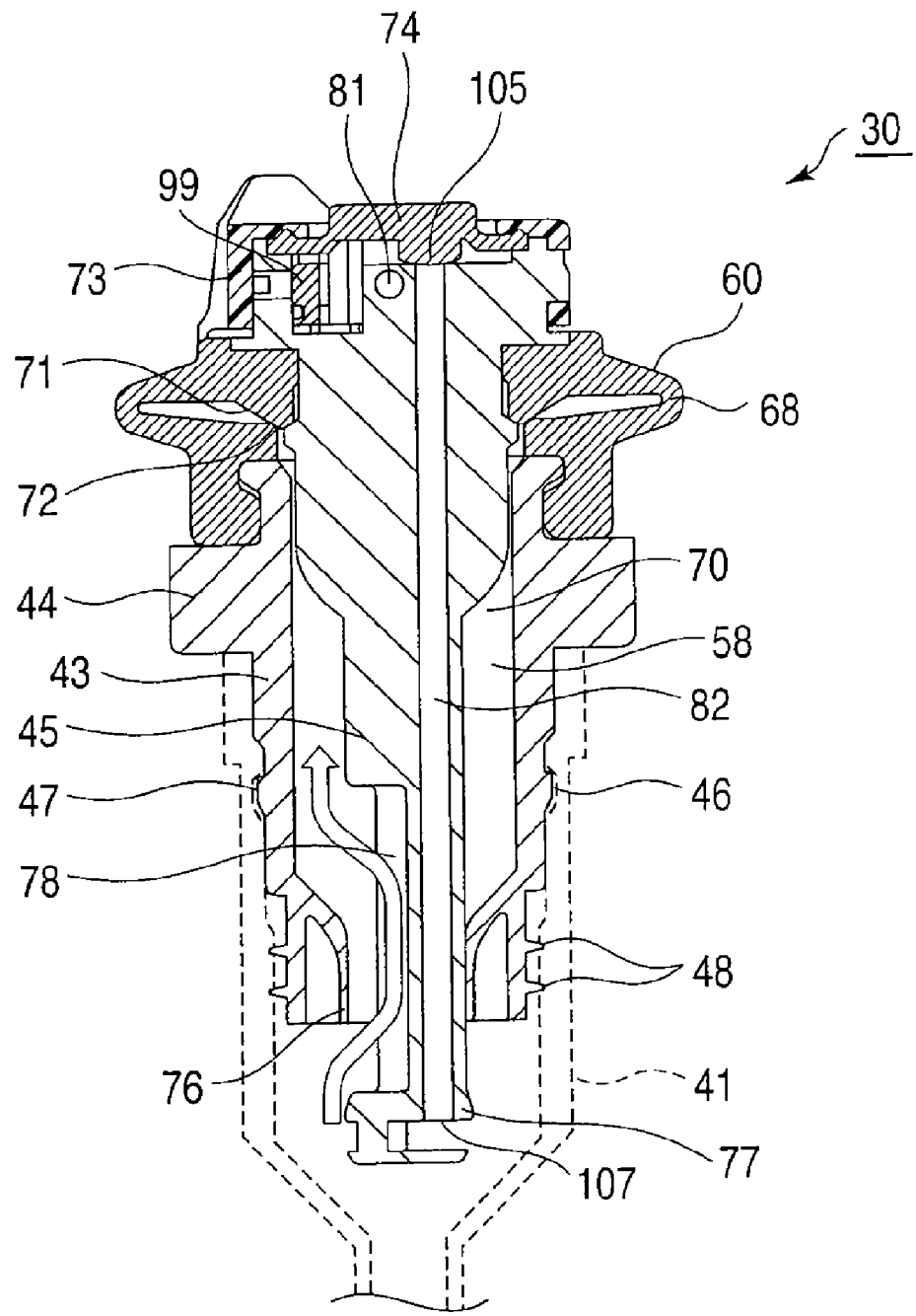
FIG. 23B is a longitudinal sectional view illustrating the fluid control apparatus, longitudinally cut along the plane along the line 4-4 in FIG. 3 during suction.
Figure 23C:
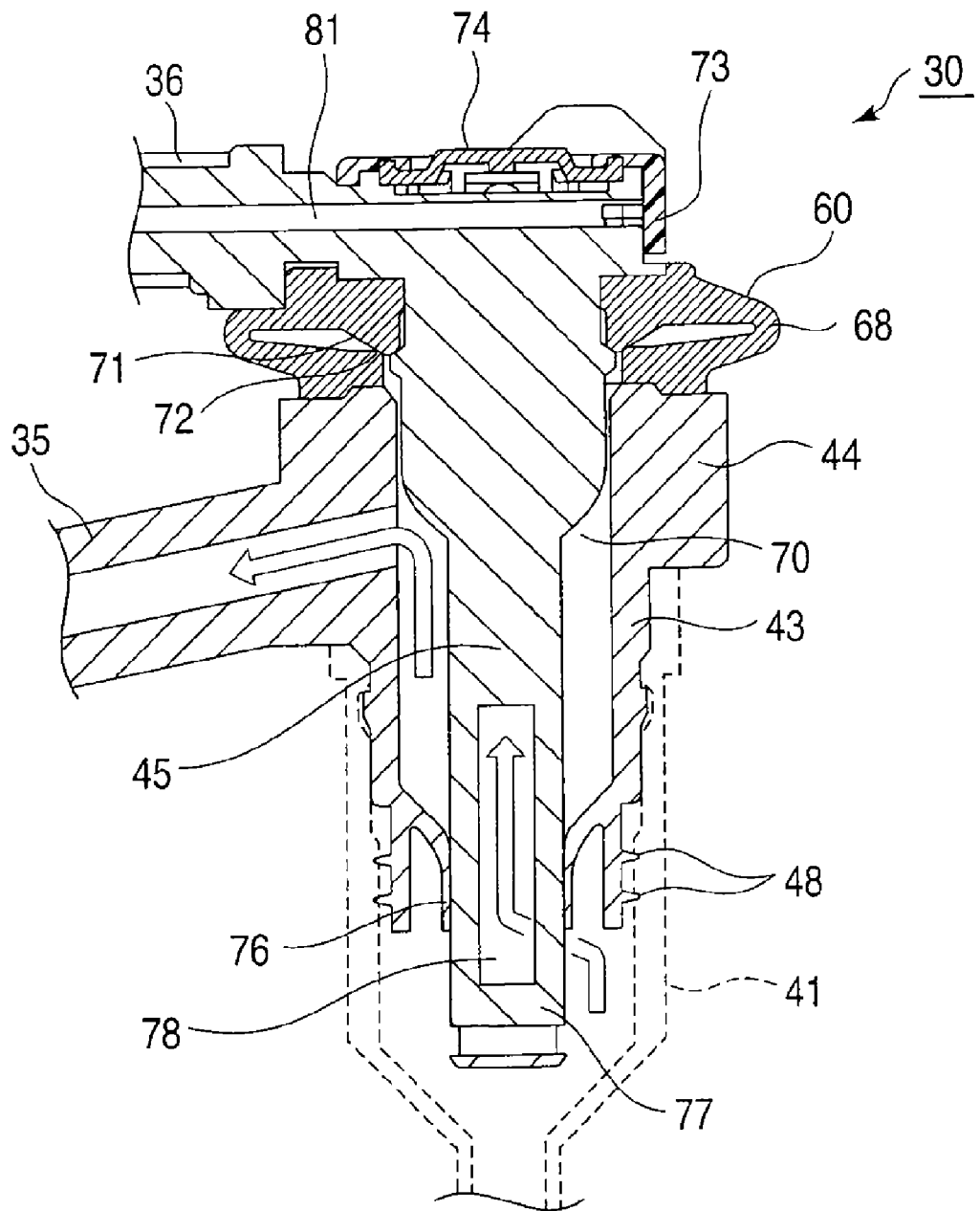
FIG. 23C is a longitudinal sectional view illustrating the fluid control apparatus, longitudinally cut along the plane along the line 3-3 in FIG. 5 during suction.

As illustrated in FIGS. 23A, 23B, and 23C, a side wall part of a middle part of the elastic member 60 is folded so as to protrude outward, and forms a spring member which can be elastically compressed and deformed in axial directions. Further, as illustrated in FIG. 3, suction leak holes 68 which communicate with the inside of the cylinder 43 (the suction channel 58 as the first channel) are drill in the side wall part of the middle part of the elastic member 60. The suction leak holes 68 communicate with the suction channel 58, and take in air from outside into the cylinder 43. Here, plural or, for example, two suction leak holes 68 are provided symmetrically in relation to a center of the elastic member 60. Further, one of the suction leak holes 68 is positioned, as illustrated in FIG. 3, between the metal suction mouthpiece 35 and the metal air-feed mouthpiece 36, at the same side portion as the metal suction mouthpiece 35 and the metal air-feed mouthpiece 36. As illustrated in FIGS. 23A, 23B, and 23C, when the elastic member 60 is pushed in together with the piston body 45, the side wall part in the middle part where the suction leak holes 68 are formed are folded so as to protrude outward. The suction leak holes 68 are thereby substantially closed. As illustrated in FIG. 3, the lower end of the elastic member 60 has a cylindrical shape, and a center part of the lower end is open. The lower end engages with the top end of the cylinder 43. Further, as described previously, the elastic member 60 also has a cylindrical shape, and a center part of the top end is open. The opening part engages with an outer circumference of the piston body 45.

As illustrated in FIGS. 3 and 4, in the opening part of the center part of the top end of the elastic member 60, a sealing surface 71 is formed on an inner surface of a top end wall part, which makes contact with the opening part and is adjacent to the opening part, so as to turn around a circumferential edge of the opening part about an axis thereof. The sealing surface 71 protrudes in a downward axis direction and has a tapered shape which is inclined in an inward radial direction. Further, in the opening part of the center part of the lower end of the elastic member 60, an edge part 72 is formed on an inner surface which is adjacent to the opening part. The edge part 72 protrudes so as to turn around along the circumferential edge of the opening part about an axis thereof. As illustrated in FIG. 23A, FIG. 23B, and FIG. 23C, when the elastic member 60 is compressed, the sealing surface 71 makes contact with the edge part 72. Further, the sealing surface 71 and edge part 72 shut off communication between inside of the cylinder 43 (the suction channel 58 as the first channel) and outside of the elastic member 60 (the suction leak holes 68). The sealing surface 71 and edge part 72 function as a valve which opens/closes at the time of suction operation.

Thus, the elastic member 60 holds the piston body 45 to be movable relatively to the cylinder 43 between the position where the suction channel 58 is closed and the position where the suction channel 58 is opened.

As illustrated in FIG. 3, the piston body 45 is formed by a member having a substantially circular columnar shape. The piston body 45 is provided in a state in which the piston body 45 substantially penetrates both of the elastic member 60 and the cylinder 43. The top end of the piston body 45 is provided so as to protrude upward from the opening part in the top end of the elastic member 60. A cover member 73 which covers a side circumferential edge of the top end of the piston body 45 is provided to cover the top end of the piston body 45 protruding from the top end of the elastic member 60. A center of the cover member 73 is open. A top end surface of the piston body 45 corresponding to the opening part is covered with an operation button (operation member) 74. The operation button 74 is a member separate from the cover member 73, and constitutes a suction manipulation part. The operation button 74 is formed of a substantially disc-like elastic member in a film-like shape. This elastic member is made of, for example, an elastic material such as rubber or thermoplastic resin. As illustrated in FIG. 3, a convex 75*a* is provided on an upper surface of an outer circumferential edge of the operation button 74, over a whole circumference thereof. A concave 75*b* is provided in a lower surface of an inner circumferential edge of the cover member 73, over a whole circumference thereof. The convex 75*a* engages with the concave 75*b* from below, thereby air-tightly connecting the cover member 73 and the operation button 74 to each other. Further, parts of the cover member 73 and operation button 74 may be fixed to each other by bonding. Although details will be described later, the cover member 73 is provided on the piston body 45. Therefore, the operation button 74 is provided, by the cover member 73, on the piston body 45 as an insertion member into which a second divisional air-feed channel 82 is inserted.

By pressing the operation button 74 or by releasing a pressure thereon, the piston body 45 can be moved in axial directions, relative to the cylinder 43, while receiving an elastic force of the elastic member 60. The elastic member 60 comes to have an elastic compression force and an elastic energizing recovery force as the piston body 45 moves. The elastic member 60 deforms in accordance with movement of the piston body 45. That is, as illustrated in FIG. 3, the suction leak holes 68 are open in a non-operational state in which the operation button 74 is not operated (this position is also referred to as a leak position). Further, as illustrated in FIGS. 23A, 23B, and 23C, when the operation button 74 is pressed and operated and the elastic member 60 is compressed, the suction leak holes 68 are substantially deformed to thereby bring the sealing surface 71 and the edge part 72 into contact with each other, thereby closing the space therebetween (this position is also referred to as a suction position).

The piston body 45 comprises a large diameter part 45*a* in a side of the top end thereof, and a small diameter part 45*b* in a side of the lower end thereof, as illustrated in FIG. 3. When the piston body 45 is at a non-operational position as illustrated in FIG. 3, the large diameter part 45*a* is located substantially outside the cylinder 43. An outer diameter of the large diameter part 45*a* is smaller than a diameter of the opening part of the center part of the lower end of the elastic member 60. Therefore, a gap is formed between the large diameter part 45*a* and the lower end of the elastic member 60. Therefore, as illustrated in FIG. 3, when the piston body 45 is at the non-operational position, a suction leak channel 70 which connects the inside of the cylinder 43 (the suction channel 58 as the first channel) to the suction leak holes 68 is formed in the gap formed between the large diameter part 45*a* and the lower end of the elastic member 60.

Further, as illustrated in FIG. 3, a valve body 77 which cooperates with a valve seat 76 formed at the lower end of the cylinder 43 is provided at the lower end of the piston body 45. The valve seat 76 and the valve body 77 form a valve part which closes when suction is not performed. The lower end of the cylinder 43 has a tapered shape which is slightly inclined downward from an inner circumferential surface in an axial direction and inward in a radial direction. In the tapered part, the lower end has a cylindrical shape which has a small diameter and is coaxial to the cylinder 43. The valve seat 76 is formed on the cylindrical inner surface. Further, as illustrated in FIG. 3, when the piston body 45 is at the non-operational position (leak position), the valve body 77 is provided inside the valve seat 76, and seals an inner hole of the valve seat 76. In addition, the valve body 77 together with the valve seat 76 shuts off the inside of the attachment tube 41 inside of the cylinder 43 (the suction channel 58 as the first channel) from each other. That is, the suction channel 58 closes.

As illustrated in FIGS. 23A, 23B, and 23C, when the piston body 45 is pressed to the suction position, the valve body 77 is positioned below the valve seat 76, at the release position indicating a position inside the attachment tube 41. At this time, the inside of the attachment tube 41 and inside of the cylinder 43 (the suction channel 58 as the first channel) communicate with each other. That is, the suction channel 58 opens.

That is, the piston body 45 comprises a valve part (valve body 77) which is movable relative to the cylinder 43 between a position where the suction channel 58 is opened relative to the insertion channel 25 and a position where the suction channel 58 is closed relative to the insertion channel 25.

As illustrated in FIGS. 3 and 4, a guide part 78 shaped like a concave groove is formed in a side wall of the piston body 45 above the valve body 77. The guide part 78 extends in an axial direction of the piston body 45 from a top end of the valve body 77. As illustrated in FIG. 3, when the piston body 45 is at the non-operational position, the entire guide part 78 is located in the cylinder 43. As illustrated in FIGS. 23A, 23B, and 23C, when the piston body 45 is pushed in to the suction position, the guide part 78 is located over the whole valve seat 76 from below to above the valve seat 76, and makes the inside of the attachment tube 41 and the inside of the cylinder 43 (the suction channel 58 as the first channel) communicate with each other to make a suction force act on the channel 28. That is, the guide part 78 makes the inside of the attachment tube 41 and the inside of the cylinder 43 (the suction channel 58 as the first channel) communicate with each other. The valve body 77 cooperates with the valve seat 76 to constitute a valve part which opens/closes the suction channel 58 as the first channel, in accordance with a moving position of the piston body 45.

As illustrated in FIG. 3, a limiter part 80 is formed on an outer circumferential surface of the lower end of the piston body 45. The limiter part 80 makes contact with a limit surface 79 constituted by a lower end surface of the valve seat 76, thereby limiting upward movement of the piston body 45. The limiter part 80 as described above is a large diameter part protruded in radial directions of the lower end of the piston body 45. Further, as illustrated in FIG. 3, when the piston body 45 is at the non-operational position where upward movement of the piston body 45 is limited, the limiter part 80 makes contact with the limit surface 79 thereby to limit upward movement of the piston body 45. When the piston body 45 is at the non-operational position where upward movement is limited, the elastic member 60 is slightly compressed/deformed in axial directions thereof. In other words, a termination end to which the piston body 45 is moved upward by an energizing force of the elastic member 60 is a position illustrated in FIG. 3, to which upward movement of the piston body 45 is limited by contact of the limiter part 80 with the limit surface 79. As illustrated in FIG. 3, when the piston body 45 is at the non-operational position, a suction leak state is created in which the suction leak holes 68 communicate with the metal suction mouthpiece 35 through a suction leak channel 70. Further, as illustrated in FIGS. 23A, 23B, and 23C, when the piston body 45 is pressed, the suction leak channel 70 closes, and the suction tube 38 is accordingly put in a suction state in which the suction tube 38 communicates with the attachment tube 41 and channel 28 through the metal suction mouthpiece 35, suction channel 58, and guide part 78. That is, the valve seat 76, valve body 77, limit surface 79, and limiter part 80 constitute a suction control mechanism.

Next, an air-feed control mechanism of the fluid control apparatus 30 will be described. As illustrated in FIG. 5A, a first divisional air-feed channel 81 which communicates with the inner hole of the metal air-feed mouthpiece 36 is provided at the top end of the piston body 45, so as to cross the top end. Further, as illustrated in FIG. 4 and FIG. 5A, a second divisional air-feed channel 82 is provided in the piston body 45, so as to penetrate the piston body 45 along vertical axis directions thereof. The piston body 45 is an insertion member into which the second divisional air-feed channel 82 is inserted. The first divisional air-feed channel 81 and second divisional air-feed channel 82 are provided in the piston body 45, so as to neither encounter each other nor directly cross each other. The first divisional air-feed channel 81 and second divisional air-feed channel 82 constitute a second channel which communicates with the metal air-feed mouthpiece 36 connecting the air-feed tube 39. That is, the piston body 45 comprises the first divisional air-feed channel 81 and second divisional air-feed channel 82, constituting a second channel which transfers fluid from the connection port part (the metal air-feed mouthpiece 36) to the insertion channel 25. Further, the piston body 45 comprises a connection port part (the metal air-feed mouthpiece 36) for connecting a fluid tube (the air-feed tube 39).

As illustrated in FIG. 5A, the first divisional air-feed channel 81 linearly communicates with the inner hole of the metal air-feed mouthpiece 36. A first communication channel 84 is formed in the side wall surface of the top end of the piston body 45. The first communication channel 84 is a groove-like notch (opening) along a circumferential direction of the piston body 45 covered with the cover member 73. The first divisional air-feed channel 81 is connected to the first communication channel 84, crossing the top end of the piston body 45. The first communication channel 84 is covered with the cover member 73, and is formed along the circumferential direction of the piston body 45 in this state. The first communication channel 84 is open toward the air-feed leak hole 85 described later. The first communication channel 84 is arranged in a manner such that the opening thereof is oriented to face the air-feed leak hole 85 and penetrates to the exterior. Therefore, resistance of air flow which leaks from the air-feed leak hole 85 decreases and improves the air-feed leak performance.

As illustrated in FIGS. 3 and 4, the cover member 73 is made of an elastic material, such as rubber or thermoplastic resin. The cover member 73 comprises an annular part 73a which covers a peripheral part of a top surface of the piston body 45, and an annular part 73b which covers a top end of a side surface of the piston body 45. The annular parts 73a and 73b are attached so as to tightly engage with the peripheral part of the top end of the piston body 45. Further, as illustrated in FIGS. 4 and 5A, a protrusion 63 is provided on the side surface of the top end of the piston body 45. A hole 64 corresponding to the protrusion 63 is provided in the cover member 73. As the protrusion 63 is engaged into the hole 64, the cover member 73 is fixedly attached to and made to be in contact with the piston body 45.

As illustrated in FIG. 5A, a finger receiver surface 86 is formed on a circumferential edge of the cover member 73. An air-feed leak hole 85 for releasing the first communication channel 84 to the exterior is provided in the finger receiver surface 86. To facilitate operation, the finger receiver surface 86 is formed so as to face the piston body 45 in press axis directions, and to be oriented downward obliquely to the press axis directions. In this manner, there is avoided that the piston body 45 is pressed under a pressing force when a finger is placed on the finger receiver surface 86. Further, a pad of the finger is put on the finger receiver surface 86, and the air-feed leak hole 85 closes accordingly. Then, leakage of a gas from the first communication channel 84 is shut off. In addition, a leakage rate of the gas can be adjusted depending on an extent to which the air-feed leak hole 85 is closed with the finger.

As illustrated in FIG. 5A, a second communication channel 88 which communicates with the first communication channel 84 through the air-feed leak hole 85 is formed at the top end of the piston body 45. The second communication channel 88 is provided in a side opposite to the first communication channel 84 in relation to the air-feed leak hole 85 interposed therebetween. Further, a direction of a flow path toward the air-feed leak hole 85 from the first communication channel 84 and a direction of a flow path toward the second communication channel 88 from the air-feed leak hole 85 cross each other. The air-feed leak hole 85 is formed near a cross point between both directions. The first communication channel 84 and second communication channel 88 cross each other at the air-feed leak hole 85, and are formed to be oriented in opposite directions to each other. Therefore, the direction of the flow path from the first communication channel 84 toward the air-feed leak hole 85 is a direction which penetrates the air-feed leak hole 85 directly to the exterior. The second communication channel 88 is formed to extend from the exterior to the inside of the air-feed leak hole 85. When the air-feed leak hole 85 is closed by an obstacle such as a finger, the obstacle can be assumed to be, namely, a mirror. In this case, light traveling from the first communication channel 84 toward the air-feed leak hole 85 is reflected by the obstacle. The first communication channel 84 and second communication channel 88 are formed in a manner such that a flow-in end of the second communication channel 88 is positioned in a reflecting direction thereof. That is, the first communication channel 84 and the second communication channel 88 are provided, in respectively opposite sides, with the air-feed leak hole 85 intervened therebetween in a manner such that the channels are reversed and bent by the air-feed leak hole 85. Further, the first communication channel 84 and second communication channel 88 are located in a manner such that an angle between a flow path from the first communication channel 84 toward the air-feed leak hole 85 and a flow path from the air-feed leak hole 85 toward the second communication channel 88 is substantially 90°. The air-feed leak hole 85 is positioned at this reverse point.

Further, as illustrated in FIG. 5A, the second communication channel 88 comprises an upstream groove 88a formed on an outer surface of the top end of the piston body 45, and a downstream hole 88b drill in the top end of the piston body 45. The downstream hole 88b is continuous to a concave hole 89 formed in the outer surface of the top end of the piston body 45. As illustrated in FIG. 4, the hole 89 is formed so as to communicate with a third communication channel 91 which is formed between the top end surface of the piston body 45 and an inner surface of the operation button 74. Further, the third communication channel 91 communicates with the first communication channel 84 through the second communication channel 88 and air-feed leak hole 85, and also communicates with the second divisional air-feed channel 82 in a manner described later.

As illustrated in FIGS. 3, 4, and 5A, the first divisional air-feed channel 81, first communication channel 84, air-feed leak hole 85, second communication channel 88, third communication channel 91, and second divisional air-feed channel 82 constitute an air-feed channel which communicates with the insertion channel 25 and channel 28, as one channel.

Figure 5B:
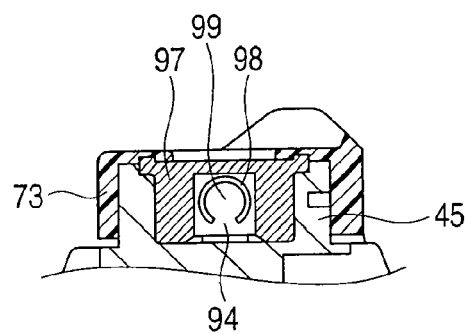
FIG. 5B is a longitudinal sectional view cut along a line 5B-5B in FIG. 5A.

As illustrated in FIGS. 5A and 5B, a check valve 95 as a first valve which stops backflow of fed air is provided between the second communication channel 88 and the third communication channel 91. That is, the check valve 95 as the first valve is provided on the air-feed channel described above, and opens only when feeding air. The check valve 95 comprises a valve seat 96 formed on a wall surface of the second communication channel 88 in the hole 89, an elastic member 97 engaged in the hole 89, and a valve body 99 formed by cutting a notch 98 in the elastic member 97. As illustrated in FIG. 5B, the notch 98 is cut in the elastic member 97 into a shape like an arc or "C", which partially acts as a hinge 94, thereby forming the valve body 99 in a shape like a flap. The elastic member 97 is engaged in the hole 89 which is drill in the top end surface of the piston body 45. The valve seat 96 is positioned in an upstream side of the air-feed flow, so as to face a valve body 99 positioned in a downstream side thereof, and puts the valve body 99 in a state of being elastically pushed into contact with the valve seat 96. Accordingly, the check valve 95 does not hinder air-feed flow in a forward direction but hinders only air-feed flow in a backward direction.

As illustrated in FIG. 5B, the valve body 99 is substantially C-shaped. The valve body 99 has a greater surface area than the notch 98. When backward flow occurs at the check valve 95, a fluid pressure acting on the valve body 99 is greater than channel resistance of the notch 98, and the valve body 99 moves like a flap, to make contact with the valve seat 96. Accordingly, the check valve 95 does not hinder air-feed flow in a forward direction but hinders only air-feed flow in a backward direction.

The hinge 94 which supports the valve body 99 is positioned to be oriented in a direction of pushing in the piston body 45, i.e., in a lower side of the valve body 99. Therefore, when the piston body 45 is pushed in, a force of pushing down the piston body 45 is applied to the elastic member 97. Even if the elastic member 97 is deformed, the force of pressing down and influence from the deformed elastic member 97 hardly transfer to the valve body 99 through the hinge 94. Further, a pressure applied to the elastic member 97 is received by a bottom surface of the hole 89, and is therefore shut off and hardly transfers to the valve body 99. Therefore, the valve body 99 is neither compressed nor twisted; and an open/close operation of the valve body 99 is stabilized by pushing in the piston body 45.

As illustrated in FIGS. 3, 4, and 5A, the check valve 95 as the first valve is positioned in an upstream side of air-feed than a valve body part 105 as a second valve, in the first divisional air-feed channel 81, first communication channel 84, air-feed leak hole 85, second communication channel 88, third communication channel 91, and second divisional air-feed channel 82, as an air-feed channel. In this manner, a suctioned material is prevented from flowing into the air-feed channel in a side of the air-feed tube.

The valve body 99 is provided on the piston body 45 as the insertion member.

As illustrated in FIG. 3, the top end surface of the piston body 45 is covered to be air-tight to the exterior by the cover member 73 and operation button (operation member) 74. Further, when the operation button 74 illustrated in FIGS. 3 and 4 is not pushed in, a third communication channel 91 is maintained in a gap between an inner surface of the operation button 74 and the top end surface of the piston body 45, on an inner surface of the operation button 74, as illustrated in FIG. 4. The third communication channel 91 communicates with the second divisional air-feed channel 82 which is open, at one end, in the top end of the piston body 45.

Further, as illustrated in FIG. 4, a valve device as the second valve capable of shutting off the third communication channel 91 and second divisional air-feed channel 82 when performing the suction operation is provided between the operation button 74 and the piston body 45. That is, as illustrated in FIG. 4, the operation button 74 comprises a convex valve body part 105 which faces the second divisional air-feed channel 82. The valve body part 105 as the valve device protrudes from the inner surface of the operation button 74. The valve body part 105 is apart from the second divisional air-feed channel 82 in a normal state in which the operation button 74 is not pushed in. When the operation button 74 is pushed in during a suction operation, the valve body part 105 makes contact with the second divisional air-feed channel 82, and closes the second divisional air-feed channel 82. The operation button 74 may directly close the second divisional air-feed channel 82 with the inner surface of the operation button 74, in place of the valve body part 105. That is, the operation button 74 may also serve as a valve body part (valve device). Thus, when the suction operation is performed, the inner surface of the operation button 74 or valve body part 105 closes the second divisional air-feed channel 82 as the operation button 74 is pushed in. Thus, the valve device (the valve body part 105 and operation button 74) as the second valve is provided on the operation button 74. When the operation button 74 is operated, the valve device functions as a check valve which shuts off communication between the first divisional air-feed channel 81 as one of the air-feed channels and the second divisional air-feed channel 82 as the other of the air-feed channels, in the air-feed channel into which the operation button 74 is inserted. Further, the valve device (valve body part 105) as the second valve is provided on the piston body 45 as the insertion member by the operation button 74. Further, as described previously, the valve body 99 and the valve body part 105 are provided on the piston body 45.

Here, when the operation button 74 is in the stand-by state, the gap is created between the inner surface of the operation button 74 and the top end surface of the piston body 45, as described previously. However, the inner surface of the operation button 74 may be brought into tight contact with the top end surface of the piston body 45 with a constant energizing force due to an elastic force of the operation button 74 itself. In this case, the operation button 74 is lifted up due to air pressure, thereby securely maintaining the third communication channel 91, and air can be fed from the third communication channel 91 to the second divisional air-feed channel 82. Further, if an air-feed pressure relatively lowers from a side of the first divisional air-feed channel 81 during suction or when the air-feed leak hole 85 is opened, the second divisional air-feed channel 82 is closed by the operation button 74, and the inner surface of the operation button 74 and the valve body part 105 advantageously function as a valve which shuts off communication between the first divisional air-feed channel 81 and the second divisional air-feed channel 82.

Thus, the inner surface of the operation button 74 and the valve body part 105 which serve also as a valve member are provided on the piston body 45, and shut off communication between the first divisional air-feed channel 81 and the second divisional air-feed channel 82.

Further, the valve body part 105 as the second valve is positioned in a downstream side of air-feed than the check valve 95 as the first valve, in the first divisional air-feed channel 81, first communication channel 84, air-feed leak hole 85, second communication channel 88, third communication channel 91, and second divisional air-feed channel 82, as the air-feed channel.

When the inner surface of the operation button 74 is brought into tight contact with the top end surface of the piston body 45 by an elastic force of the operation button 74 itself and air-feed is performed, the first divisional air-feed channel 81 and the second divisional air-feed channel 82 are once made to communicate with each other. Then, the pressure inside the operation button 74 suddenly decreases, and the operation button 74 contracts. Accordingly, the second divisional air-feed channel 82 is once closed by the operation button 74, and the air-feed pressure increases again. Then, the operation button 74 expands, and the second divisional air-feed channel 82 opens accordingly. Thus, expansion and contraction of the operation button 74 are repeated, and the operation button 74 then vibrates, thereby generating a sound. This sound changes depending on air-feed conditions such as an air-feed rate and an air-feed pressure. Therefore, operators can be made aware of an air-feed condition by sound, since such condition is difficult to comprehend visually.

As described previously, the second divisional air-feed channel 82 penetrates the piston body 45 in axial directions of movement of the piston body 45, as illustrated in FIG. 4. A lower end of the second divisional air-feed channel 82 forms an air-feed port 107 in a lower end surface of the piston body 45, as illustrated in FIG. 4. The air-feed port 107 is open so as to constantly communicate with the inside of the attachment tube 41. The air-feed port 107 is open perpendicularly to an extending direction of the insertion channel 25 at the lower end of the piston body 45. Therefore, it is difficult for a suctioned material to enter the second divisional air-feed channel 82.

As illustrated in FIG. 2, the suction tube connection part 57 for connecting the suction tube 38 is provided at a tip end of the metal suction mouthpiece 35.

Next, a description will be given of a first engagement part by which the elastic member 60 and the piston body 45 restrict each other from rotating, and fixedly connect (engage) the elastic member 60 and the piston body 45 so as not to rotate about the axis of the piston body 45. FIG. 6 illustrates an example of the first engagement part. The first engagement part comprises a protrusion 121 which is provided on a lower surface of a base part of the metal air-feed mouthpiece 36 extending from the top end of the piston body 45, and protruding downward from the lower surface, and a pair of engagement protrusions 122 which are provided on a side surface of the top end of the elastic member 60, corresponding to the protrusion 121, and protrude in an extending direction of the metal air-feed mouthpiece 36. The protrusion 121 is formed to be integral with the piston body 45. The engagement protrusions 122 are formed to be integral with the elastic member 60. Opposed surfaces 123 of the engagement protrusions 122 which face each other are inclined so as to widen toward lower ends. The protrusion 121 has a tip end 124 which is thick and protrudes toward the opposed surfaces 123. As illustrated in FIG. 6, when the tip end 124 is engaged between the opposed surfaces 123, the engagement protrusions 122 and the protrusion 121 securely engage each other, thus the protrusion 121 cannot come away from the engagement protrusions 122 easily. Accordingly, the piston body 45 can be fixedly connected to the elastic member 60.

The pair of engagement protrusions 122 may comprise a ring-shaped engagement part. In this case, the protrusion 121 may be engaged into the ring-shaped engagement part. Also in this case, the elastic member 60 and the piston body 45 can be fixedly connected.

In this manner, the top end of the piston body 45 and the top end of the elastic member 60 are fixedly connected to each other by the first engagement part. Therefore, when the piston body 45 is rotated about the axis thereof due to some reason, the top end of the elastic member 60 rotates together with the piston body 45.

Further, the protrusion 121 and engagement protrusions 122 are located below the metal air-feed mouthpiece 36. Therefore, the protrusion 121 and engagement protrusions 122 rarely become obstacles. The metal suction mouthpiece 35 and metal air-feed mouthpiece 36 protrude substantially in the same direction as each other. Therefore, the protrusion 121 and engagement protrusions 122 are located between the metal suction mouthpiece 35 and the metal air-feed mouthpiece 36, so that the protrusion 121 and engagement protrusions 122 obstruct neither the metal suction mouthpiece 35 nor the metal air-feed mouthpiece 36. Further, as illustrated in FIG. 6, if the suction leak hole 68 is located between the metal suction mouthpiece 35 and the metal air-feed mouthpiece 36, the metal suction mouthpiece 35 and metal air-feed mouthpiece 36 hinder, for example, hands from touching or coming close to the suction leak hole 68 as much as possible. In view of molding, a structure for parting a mold is simplified. Although the protrusion 121 is formed to be integral with the piston body 45 and the engagement protrusions 122 are formed to be integral with the elastic member 60, the protrusion 121 may be formed to be separate from the piston body 45 and the engagement protrusions 122 may be formed to be separate from the elastic member 60.

In the example of the first engagement part, the piston body 45 is directly connected to the elastic member 60. The embodiment is not limited to this example. In this case, the cover member 73 is attached, by a whirl-stop, to the top ends of the piston body 45. Further, the engagement part may fixedly engage the piston body 45 with the elastic member 60 indirectly by the cover member 73.

Figure 8:
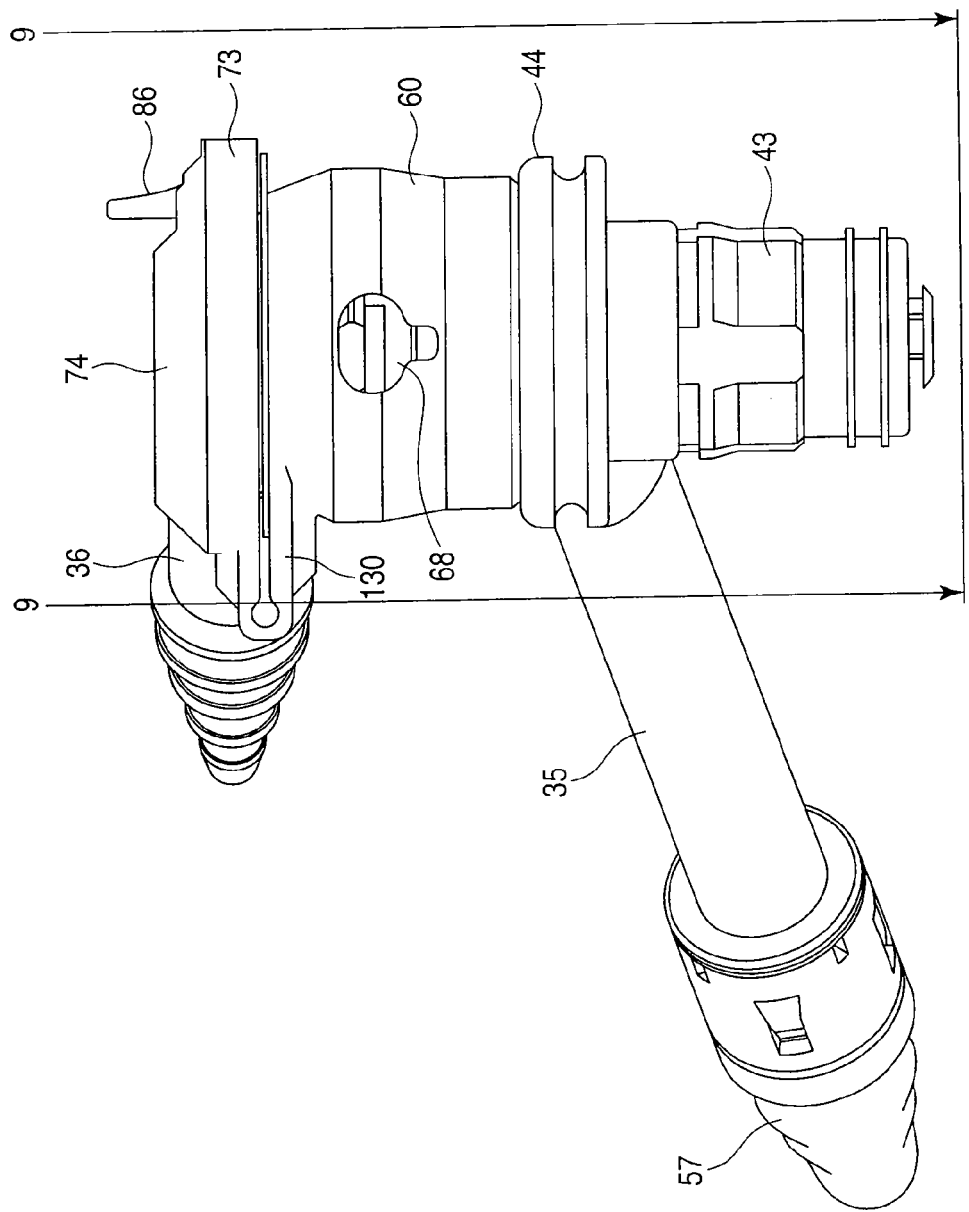
FIG. 8 is a front view of the fluid control apparatus according to another embodiment.
Figure 9:
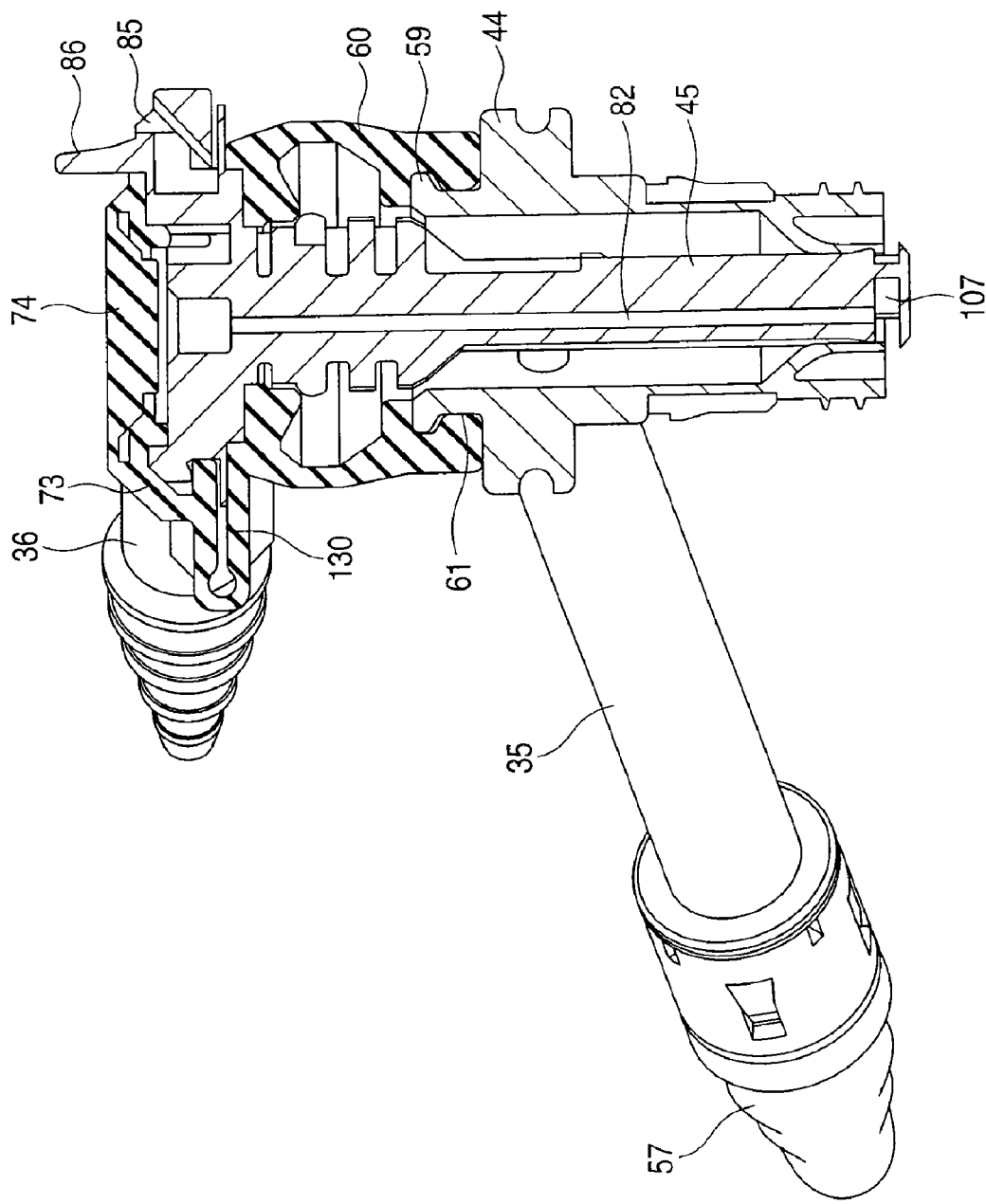
FIG. 9 is a longitudinal sectional view illustrating the fluid control apparatus, longitudinally cut along a plane along a line 9-9 in FIG. 8.

FIGS. 8, 9, and 10 illustrate an example of the first engagement part. As illustrated in FIGS. 8, 9, and 10, the top end edge of the elastic member 60 and the lower end edge of the cover member 73 are connected to each other by a connection band (connection member) 130. The connection band 130 is formed in the form of a band. An end of the connection band 130 is connected to the elastic member 60, and the other end of the connection band 130 is connected to the cover member 73. That is, the valve member (the inner surface of the operation button 74 and the valve body part 105), and the elastic member 60 are connected to each other by the connection band 130. Thus, since the valve member (the inner surface of the operation button 74 and the valve body part 105) and the elastic member 60 are connected to each other by the connection band 130, the valve member (the inner surface of the operation button 74 and the valve body part 105) and the elastic member 60 form the first engagement part which prevents the piston body 45 and the elastic member 60 from rotating about the axis of movement of the piston body 45.

The connection band 130 may form the elastic member 60 and the cover member 73 to be integral with each other. That is, the connection band 130 may be formed to be integral with the valve member (the inner surface of the operation button 74 and the valve body part 105) and the elastic member 60. In this manner, the valve member (the inner surface of the operation button 74 and the valve body part 105) and the elastic member 60 form the first engagement part, as described above. In addition, the operation button 74 can be prevented from detaching from the elastic member 60. Further, the operation button 74 is pressed, and the inner surface of the operation button 74 and the valve body part 105 accordingly shut off the third communication channel 91 and second divisional airfeed channel 82. Then the pressure directly transfers to the elastic member 60. Further, the pressure pushes in the elastic member 60 together with the piston body 45, and the suction leak hole 68 is substantially closed.

In a final stage of assembling the elastic member 60 in the piston body 45, the connection band 130 is bent and folded up. Further, a plate surface direction of the connection band 130 is perpendicular to the axis directions of the elastic member 60 and piston body 45 in order to increase the connection strength of the connection band 130.

Figure 11:
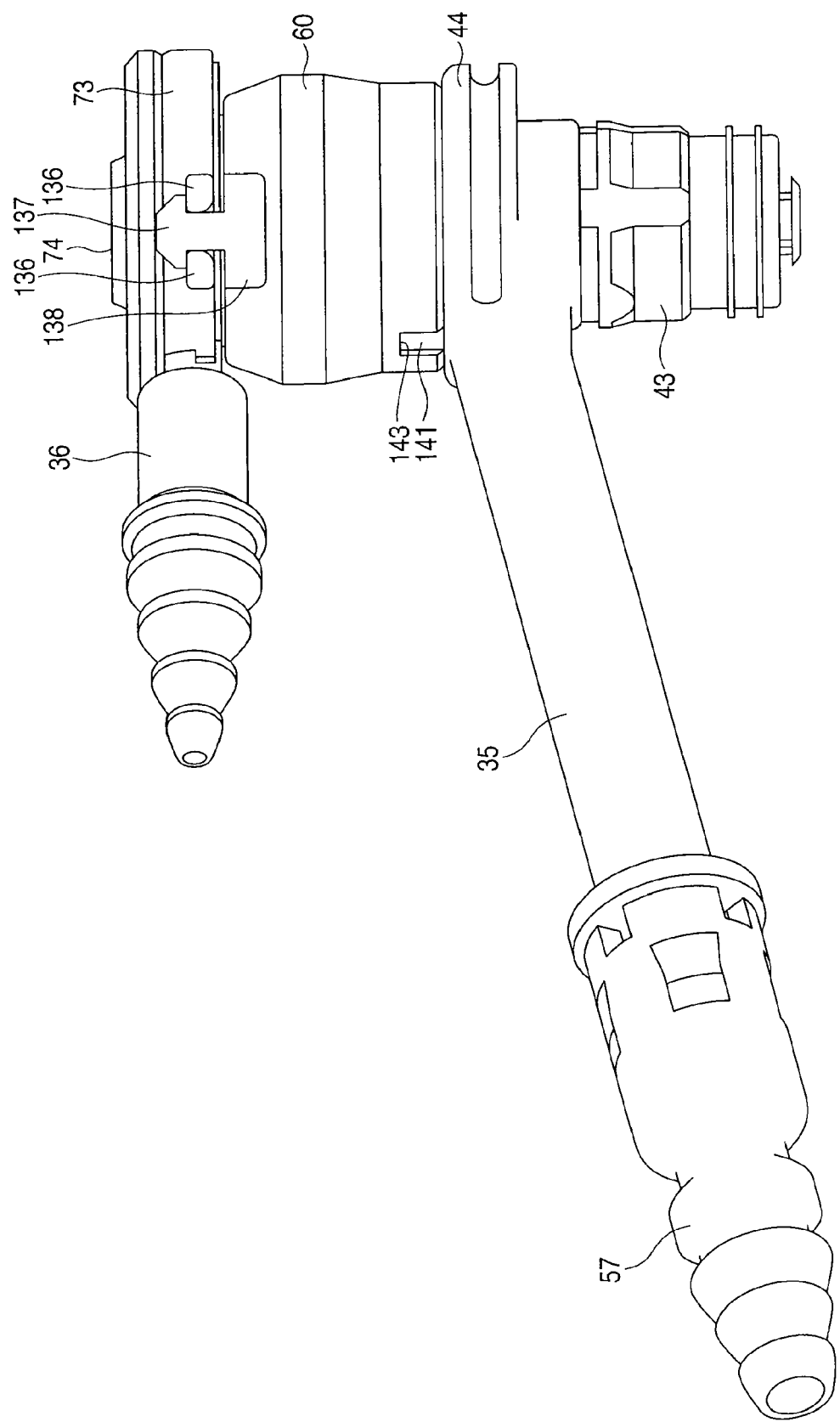
FIG. 11 is a side view of the fluid control apparatus according to still another embodiment.
Figure 12:
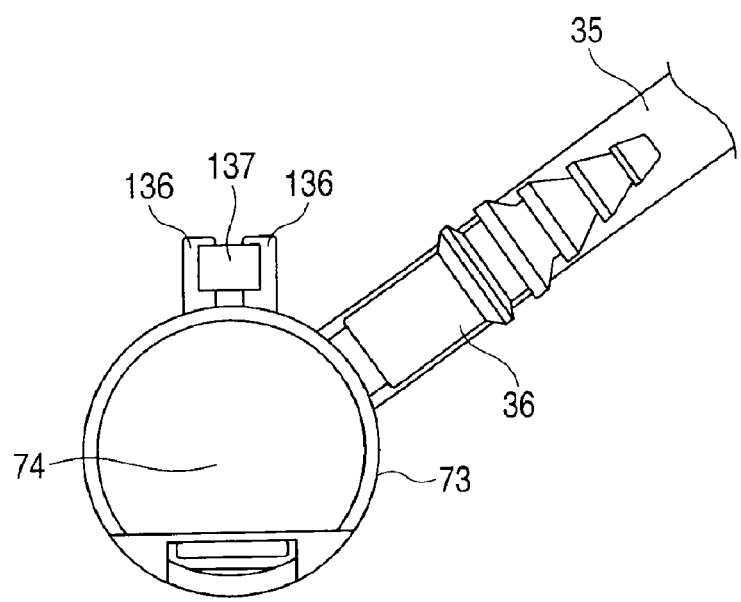
FIG. 12 is a plan view of the fluid control apparatus in FIG. 11.
Figure 13:
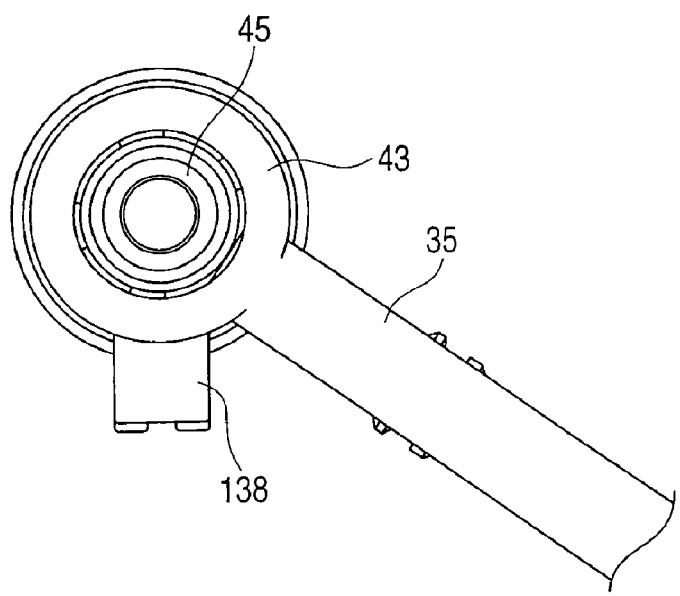
FIG. 13 is a bottom view of the fluid control apparatus in FIG. 11.

FIGS. 11, 12, and 13 illustrate another example of the first engagement part which connects the elastic member 60 and the cover member 73. The cover member 73 is provided with a pair of protrusions 136. A protrusion 137 which is engaged between the pair of protrusions 136 from below the protrusions 136 is provided at a part of a side wall surface of a top end of the elastic member 60. A protrusion 138 is formed to be integral with the elastic member 60. The protrusion 137 is formed to be integral with a top surface of the protrusion 138. The protrusion 137 is engaged between the protrusions 136. Therefore, the top end of the elastic member 60 is fixedly connected to the piston body 45. Further, the pair of protrusions 136 may be ring-shaped. In this case, the protrusion 137 is engaged in such a ring-shaped protrusion 136.

Next, a description will be made of a second engagement part by which the elastic member 60 and the cylinder 43 restrict each other from rotating, and fixedly connect (engage) the elastic member 60 and the cylinder 43 so as not to rotate about the axis of the cylinder 43. As illustrated in FIGS. 6 and 7, the second engagement part comprises two plate-like stand parts 141 which are provided to stand on parts of a top end of the flange 44 and are located to be symmetrical to each other about the axis of the cylinder 43 as a symmetry center. One of the stand parts 141 is provided just above the metal suction mouthpiece 35. On two side edges of each of the stand parts 141, flaps 142 are formed as covers which extend in circumferential directions of the cylinder 43. That is, the second engagement part comprises flaps 142 as covers which covers the stand parts 141 and engagement holes 143 as parts engaging the cylinder 43 and the elastic member 60 with each other. The flaps 142 prevent the stand parts 141 from easily falling off of the engagement holes 143 when the stand parts 141 and engagement holes 143 are engaged with each other.

Further, as illustrated in FIG. 7, the second engagement part comprises engagement holes 143 which are formed corresponding to the stand parts 141 at the lower end edge of the elastic member 60 and into which the stand parts 141 are engaged. The engagement holes 143 are formed by cutting the elastic member 60 at the lower end edge of the elastic member 60. The stand parts 141 are engaged in the engagement holes 143, and the lower end of the elastic member 60 and the cylinder 43 are fixedly connected to each other. Therefore, owing to the second engagement part, the lower end of the elastic member 60 does not rotate about the axis of the cylinder 43. Further, the flaps 142 are formed on the stand parts 141, and cover an engaging part where the stand parts 141 and engagement holes 143 are engaged with each other, as a part engaging the cylinder 43 and the elastic member 60 with each other. Therefore, the stand parts 141 are engaged in the engagement holes 143, and are hindered from easily falling out of the engagement holes 143. Also, as illustrated in FIG. 11, the flaps 142 may be formed on the stand parts 141. In this case, the elastic member 60 and cylinder 43 can be fixedly connected to each other.

Figure 14:
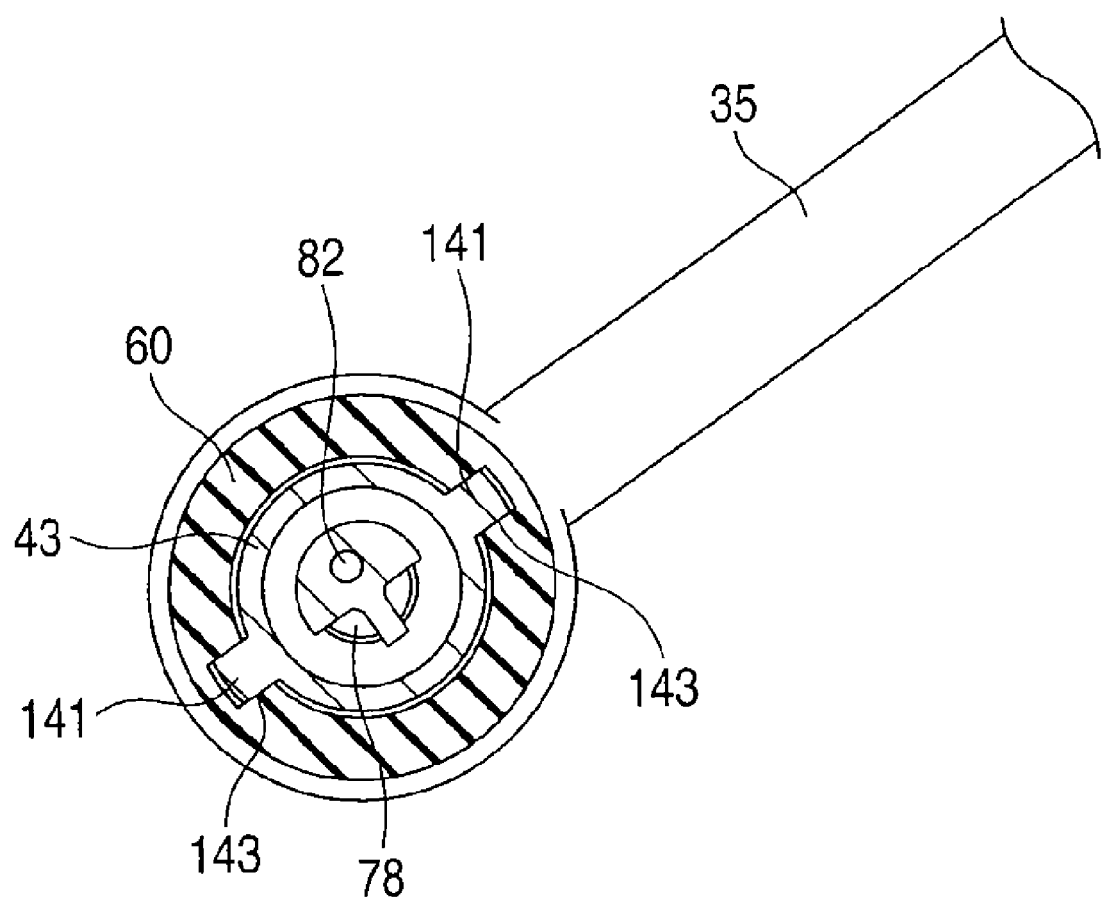
FIG. 14 is a cross sectional view laterally cut along the same position as in FIG. 7, according to still another embodiment.

Further, as illustrated in FIG. 14, in the second engagement part, the engagement holes 143 remain in a wall part of the elastic member 60, and are each formed in a groove-like shape so as not to penetrate to the exterior, to be open only to the inner surface of the elastic member 60. At this time, the stand parts 141 may have a length adequate for the engagement holes 143. In this case, the elastic member 60 has a structure such that parts of the stand parts 141 and engagement holes 143 with which the cylinder 43 is engaged are continuously closed over the whole circumference of the elastic member 60. That is, since the number of parts which are open to the exterior over the whole circumference of the elastic member 60 is reduced, the strength of the lower end of the elastic member 60 increases, and the strength of attachment to the cylinder 43 can be increased.

Figure 16A:
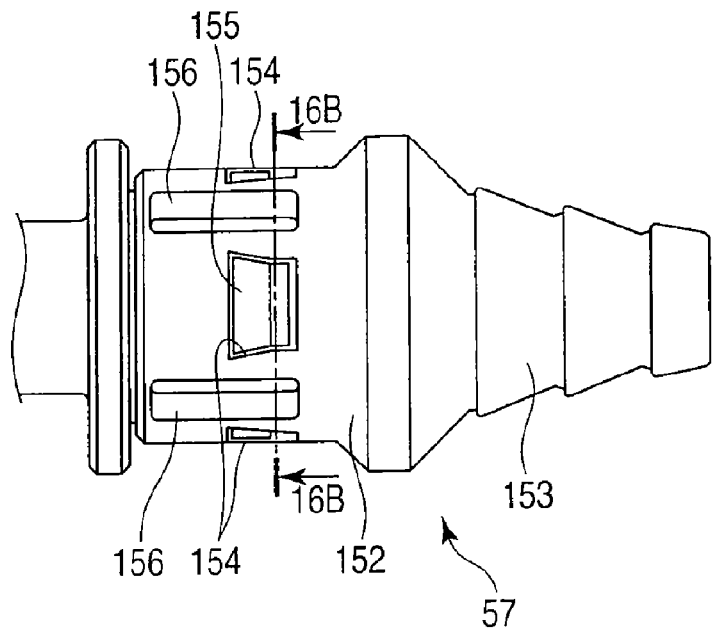
FIG. 16A is a side view illustrating the tube connection part of the metal suction mouthpiece of the fluid control apparatus.
Figure 16B:
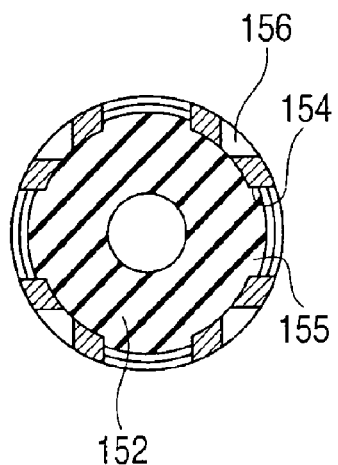
FIG. 16B is a cross sectional view cut along a line 16B-16B in FIG. 16A.

The suction tube connection part 57 for connecting the suction tube 38 is provided at the tip end of the metal suction mouthpiece 35. As illustrated in FIGS. 15A, 15B, 16A, and 16B, the suction tube connection part 57 comprises an attachment body 152 which is attachable/detachable to/from the metal suction mouthpiece 35, and a connection-part body 153 which is engaged with and connected to the suction tube 38. The attachment body 152 is formed in a substantially cylindrical shape. Plural engagement holes 154 are formed in a circumferential wall of the attachment body 152. Plural engagement protrusions 155 are formed on the tip end of the metal suction mouthpiece 35. As the engagement protrusions 155 are engaged in the engagement holes 154, a whirl-stop for the suction tube connection part 57 is formed. As illustrated in FIG. 16A, the engagement holes 154 each are formed to be inclined or tapered in a manner such that a width of each hole narrows toward the connection-part body 153, relative to axial directions. In this manner, when the engagement protrusions 155 are engaged in the engagement holes 154, positions of the engagement hole 154 are prevented from shifting even if positions of the engagement protrusions 155 shift in a rotating direction. In addition, the engagement protrusions 155 are easily engaged in the engagement holes 154. Further, plural slits 156 are provided in the circumferential wall of the attachment body 152 so that the attachment body 152 may easily deform. When the suction tube connection part 57 is engaged in the metal suction mouthpiece 35, the suction tube connection part 57 can be easily attached to the metal suction mouthpiece 35 since the suction tube connection part 57 can easily deform owing to the slits 156. The slits 156 may be formed so as to penetrate to the side of the metal suction mouthpiece 35.

Figure 17:
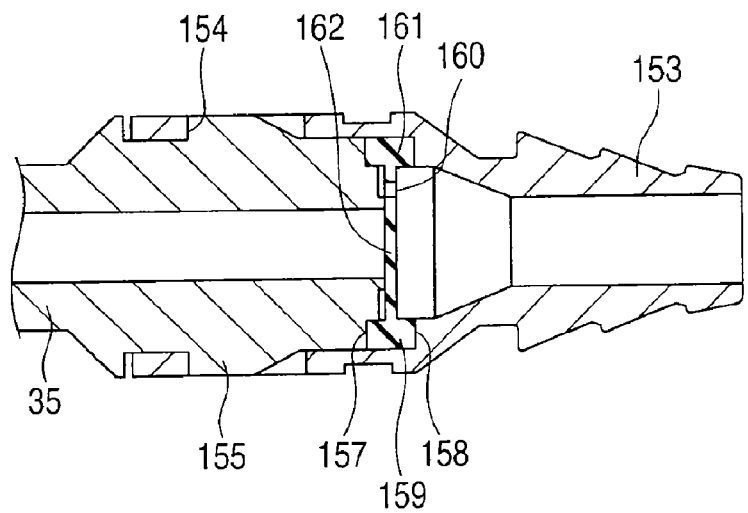
FIG. 17 is a longitudinal sectional view illustrating a part of a tube connection part of a metal suction mouthpiece in another fluid control apparatus.

As illustrated in FIG. 15A, a gasket member 159 is engaged between a protruding tip end surface 157 of the metal suction mouthpiece 35 and a step-part end surface 158 which is opposed to the protruding tip end surface 157 and is formed in the connection-part body 153. The gasket member 159 has elasticity to provide sealing between the metal suction mouthpiece 35 and the suction tube connection part 57. A circumferential edge of the gasket member 159 is formed as a flange 161 which is thicker than a center part thereof. The flange 161 is attached to be sandwiched between the protruding tip end surface 157 and the step-part end surface 158. The flange 161 is formed so as to protrude to a side of one surface of the gasket member 159 in an axis direction of the metal suction mouthpiece 35. However, as illustrated in FIG. 17, the flange 161 may be configured to protrude into sides of two surfaces thereof. In this manner, when the gasket member 159 is inserted, a direction need not be specified, and therefore, the gasket member 159 can be easily attached.

In the center part of the gasket member 159, as illustrated in FIG. 15B, a C-shaped notch 160 is formed, leaving a flap 162 uncut. The notch 160 is provided in a manner such that the flap 162 elastically makes contact with the protruding tip end surface (valve seat) 157 of the metal suction mouthpiece 35. In this manner, the flap 162 forms a check valve which allows flow of fluid being suctioned and prevents back flow. Such a check valve can be simply assembled and allows the gasket member 159 to be attached easily in a regular posture without twisting a part of the check valve.

Figure 18:
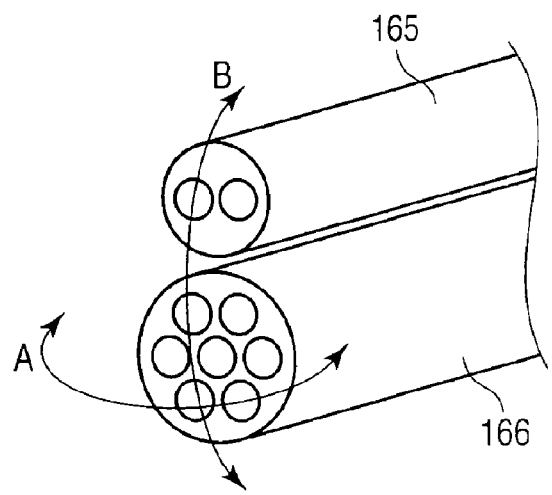
FIG. 18 is an explanatory view for imaging cables assembled in the endoscope.
Figure 21A:
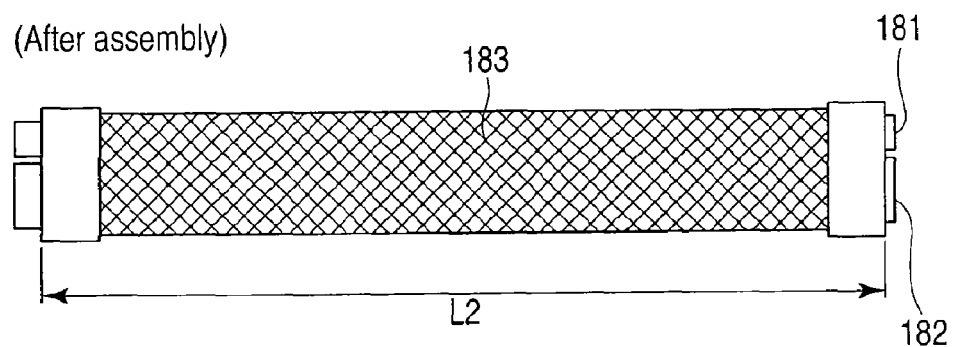
FIG. 21A illustrates a state after assembling the imaging cables in the blade, and a structure of covering the imaging cables with the blade.
Figure 21B:
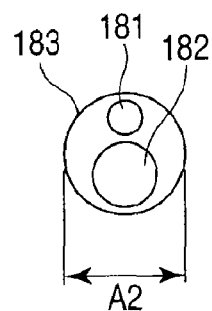
FIG. 21B is a front view of FIG. 21A.

Next, a structure of distributing imaging cables included in the endoscope insertion part 12 will be described. In general, an imaging unit for imaging an endoscopic viewfield is provided in the tip end structure 15. A number of signal lines are connected to the imaging unit. If the signal lines are bundled together into one cable, a diameter of the cable is so thick that a dead space increases in the endoscope insertion part 12 and interference with other parts occurs more easily. Based on the above, as a technique for dividing the number of signal lines to improve installation efficiency, for example, there is a case that ten signal lines are divided into a group of two signal lines and a group of eight signal lines. However, in this case, there is a drop in strength of a cable group which includes less signal lines or a cable group into which signal lines having weak output power are grouped. Accordingly, in assembly or repair, one cable group is twisted and sandwiched between an inner surface of a blade and the other cable group, and is easily made immovable. Further, as illustrated in FIG. 18, a degree of freedom is small in bending in a direction B in which a cable group 165 including two cables (signal lines) and a cable group 166 including seven cables are arranged in line, while the degree of freedom is large in bending in a direction A perpendicular to the direction B. There is a risk of causing buckling if the cable is bent in the direction B.

Hence, the technique of increasing installation efficiency of the imaging cables will be described with reference to FIGS. 19A, 19B, 19C, and 19D. In FIG. 19A, more than two cable groups 171a and 171b which include a signal line 170 are bundled by a cover material 173. There is a high risk that two ends of the cover material 173 are buckled. Therefore, rigid reinforcement wires 174 are provided at two ends of the cover material 173. The cover material 173 is assembled to be integral with the reinforcement wires 174. Further, rigid reinforcement wires 174 are provided on an extension line which connects a center of the narrower cable group 171a and a center of the thicker cable group 171b. The cover material 173 is made of, for example, thermoplastic resin or an elastic material. The structure as described above is provided from the tip end structure 15 to the inside of the universal cord 19 through the endoscope manipulation part 14 (also in a case described below).

In FIG. 19B, the cover material 173 is provided with a rigid reinforcement wire 174 in a side of the cable group 171a including less signal lines 170. The cover material 173 is assembled to be integral with the reinforcement wire 174.

In FIG. 19C, the cable groups 171a and 171b are provided in lumina 177 in a lumen tube 176. The lumen tube 176 is provided with reinforcement wire 174 in a side of the cable group 171a which includes less signal lines 170.

In FIG. 19D, the reinforcement wire 174 illustrated in FIG. 19C serves also as a rigid ground (GND) line 178. Further, when the lumen tube 176 is used, the lumina 177 is provided with a GND line 178.

Further, as illustrated in FIGS. 20A, 20B, 21A, and 21B, in the endoscope 10 comprising at least more than two imaging cables 181 and 182, the imaging cables 181 and 182 penetrate an outer cover, such as a blade 183 to cope with a radiated electromagnetic field, and are put together by the blade 183.

The blade 183 is supposed to have a length L1 before the imaging cables 181 and 182 are assembled in the blade 183, and an inner diameter of the outer cover of the blade 183 at this time is denoted as A1 (see FIG. 20A and FIG. 20B). Further, the imaging cables 181 and 182 are assembled in the blade 183, and are fixed to the blade 183 at two ends. A length dimension of the blade 183 after the fixation is expressed as L2, and the inner diameter of the blade 183 is expressed as A2 (see FIGS. 21A and 21B). At this time, settings are made to satisfy relationships of L1<L2 and A1>A2. Further, the assembled imaging cables 181 and 182 are configured not to be in tight contact with the blade 183 but to be loosely held by the blade 183 with a margin.

After assembling the imaging cables 181 and 182, the blade 183 can be extended by drawing the blade 183, and a diameter of the blade 183 narrows accordingly. At this time, adjustment is made so that the assembled imaging cables 181 and 182 may not make tight contact with the blade. In this manner, the imaging cables 181 and 182 can freely move in the blade 183, and the imaging cable 181 and 182 are accordingly restricted from being applied with an unintentional external force. Therefore, durability of the imaging cables 181 and 182 improves.

Next, operation of the endoscopic device according to the present embodiment will be described. When the endoscope 10 is used, the fluid control apparatus 30 is attached to the attachment part 32, for preparation. At this time, as illustrated in FIG. 3, the cylinder 43 is inserted into the attachment tube 41 so as to match positions of the cam part 49 and the cam receiving part 50 with each other. Also as illustrated in FIG. 3, the fluid control apparatus 30 is attached to the attachment part 32 so as to engage the convex 46 and concave 47 with each other. Next, the suction tube connection part 57 is connected to an end of the suction tube 38, and the other end of the suction tube 38 is connected to an unillustrated suction device. Further, the metal air-feed mouthpiece 36 is connected to an end of the air-feed tube 39, and the other end of the air-feed tube 39 is connected to an unillustrated air-feed device.

Thus, when the fluid control apparatus 30 is attached to the attachment part 32, as illustrated in FIG. 23A, the finger receiver surface (air-feed operation surface) 86 where the air-feed leak hole 85 is open is located at a different position from the metal air-feed mouthpiece 36 to which the suction tube 38 is connected, and from the metal suction mouthpiece 35 to which the suction tube 38 is connected. Further, the finger receiver surface (air-feed operation surface) 86 is apart from the suction leak hole 68. As a result of this, the finger receiver surface (air-feed operation surface) 86 makes as little interference as possible with other constitutive members, and the air-feed leak hole 85 can therefore be easily operated by an operator's finger.

Next, a non-operational state of the fluid control apparatus 30 will be described. As illustrated in FIGS. 3, 4, and 5A, the fluid control apparatus 30 is in a stand-by state. When the suction device is driven, external air is taken in through the suction leak holes 68 into the fluid control apparatus 30 since the suction channel 58 and the suction leak channel 70 communicate with the suction leak holes 68. At this time, the valve part constituted by the valve seat 76 and valve body 77 is closed, and communication with the channel 28 (insertion channel 25) is shut off. Accordingly, suction from a side of the insertion channel 25 is prevented. Further, as denoted by arrows in FIG. 3, air taken in from the suction leak holes 68 is suctioned through the metal suction mouthpiece 35 and suction tube 38 by the suction device.

Further, when the air-feed device is driven, as denoted by an arrow in FIG. 5A, compressed air is fed into the metal air-feed mouthpiece 36 through the air-feed tube 39. The compressed air fed to the metal air-feed mouthpiece 36 flows from the first divisional air-feed channel 81 through the first communication channel 84 to the air-feed leak hole 85, and leaks to the exterior from the air-feed leak hole 85. Due to this leakage, an air-feed pressure at the air-feed leak hole 85 decreases, and the compressed air is therefore not fed to a side of the second communication channel 88. Thus, the compressed air is not fed to the side of the second communication channel 88, and the valve body 99 does therefore not open. Accordingly, the compressed air is not fed from the third communication channel 91 to the second divisional air-feed channel 82. Accordingly, air-feed to the insertion channel 25 is not performed.

Next, a description will be made of a case in which suction and air-feed are controlled by the fluid control apparatus 30. When the endoscope 10 is used, normally, the endoscope insertion part 12 is gripped by one hand, and the endoscope manipulation part 14 is gripped by the other hand. On the hand which grips the endoscope manipulation part 14, the endoscope grip part 22 is held by three fingers except a thumb and an index finger. The bend lever 24 is operated by the thumb of this hand, and the fluid control apparatus 30 is operated by the index finger of this hand. That is, the operation button 74 and air-feed leak hole 85 are operated by the index finger of the hand which grips and operates the endoscope manipulation part 14.

Figure 22A:
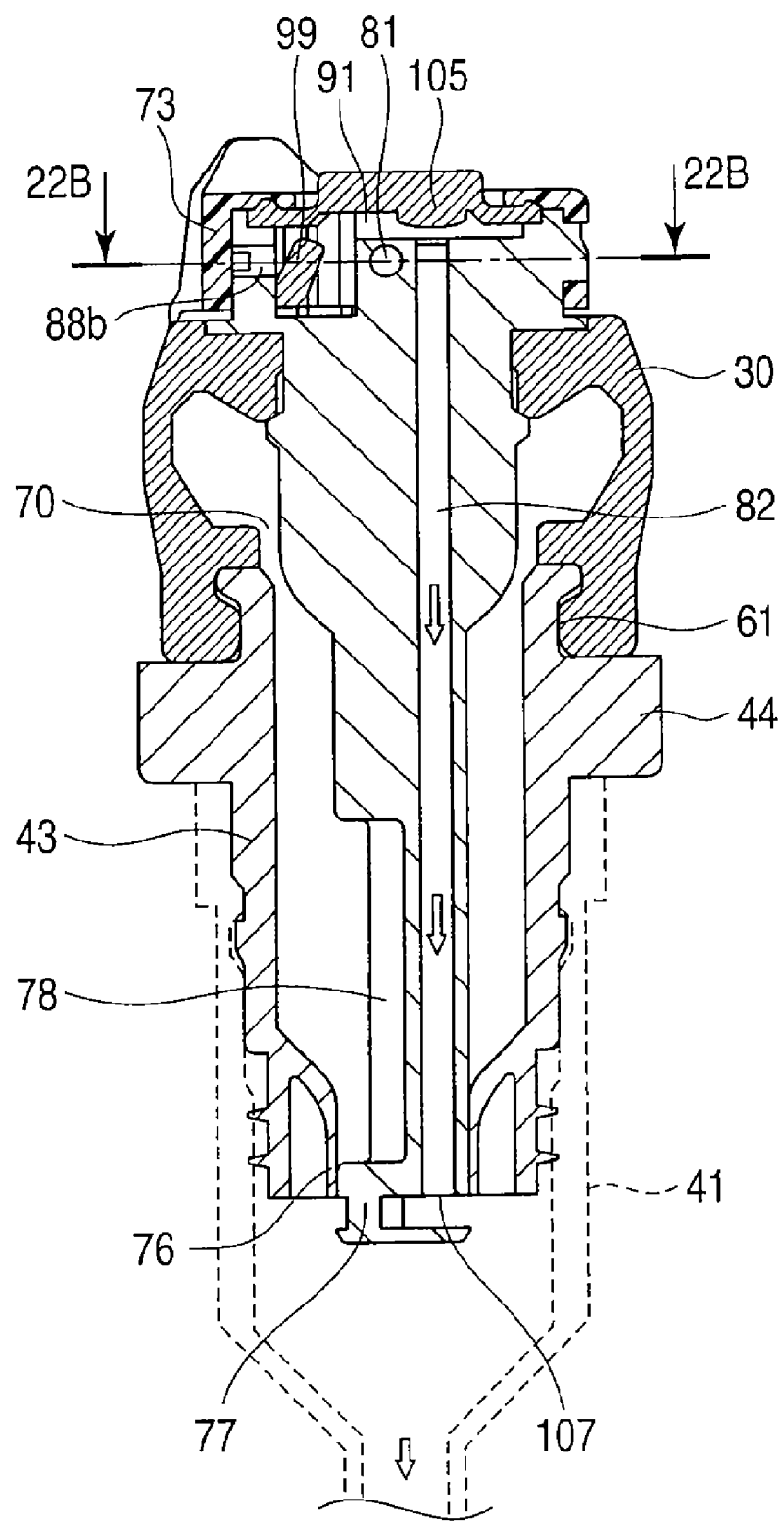
FIG. 22A is a longitudinal sectional view illustrating the fluid control apparatus, longitudinally cut along the plane along the line 4-4 in FIG. 3 during air feed.
Figure 22B:
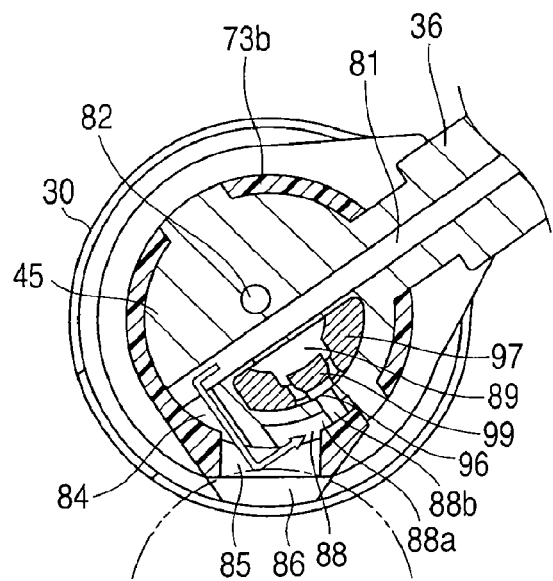
FIG. 22B is a cross sectional view cut along a line 22B-22B in FIG. 22A.

At first, a description will be made of a case in which the fluid control apparatus 30 controls air-feed. As illustrated in FIG. 22B, a pad of the index finger is brought into contact with the finger receiver surface 86, thereby closing the air-feed leak hole 85. Then, a gas (compressed air) which has been leaking to the exterior through the air-feed leak hole 85 is shut off, and an air-feed pressure inside the air-feed leak hole 85 increases. In this manner, as denoted by an arrow in FIG. 22B, the gas is fed to the side of the second communication channel 88. The gas which has flowed to the side of the second communication channel 88 pushes and opens the valve body 99, as illustrated in FIG. 22A, and is fed to the third communication channel 91 through the hole 89 illustrated in FIG. 22B. At this time, the operation button 74 is not pressed but floats under a pressure of the gas fed into the third communication channel 91, as illustrated in FIG. 22A, thereby forming the third communication channel 91. Further, the gas is fed to the second divisional air-feed channel 82 through the third communication channel 91. The gas fed into the second divisional air-feed channel 82 then flows to the insertion channel 25 from the air-feed port 107 through the inside of the cylinder 43 and attachment tube 41 and through the channel 28. Further, the gas flows from the channel opening 26 into the body cavity.

Next, a description will be made of a case in which the fluid control apparatus 30 controls suction. In this case, as illustrated in FIG. 23A, the operation button 74 is pushed in a direction denoted by an arrow P. The piston body 45 thereby moves down (to the suction position) relative to the elastic member 60 and the cylinder 43. Then, as illustrated in FIGS. 23B and 23C, the elastic member 60 is pushed and compressed, and the sealing surface 71 accordingly makes contact with the edge part 72. In this manner, the sealing surface 71 and the edge part 72 shut off communication between the inside of the cylinder 43 (the suction channel 58 as the first channel) and outside of the elastic member 60 (the suction leak hole 68). Further, during suction operation, the valve body part 105 closes the second divisional air-feed channel 82, and therefore, suction from the second divisional air-feed channel 82 to the sides of the first divisional air-feed channel 81 and air-feed leak hole 85 is prevented. At this time, the side wall part of the middle part of the elastic member 60 (near the suction leak hole 68) is folded so as to protrude outward. Therefore, the suction leak hole 68 itself is pushed and compressed (see FIGS. 23A, 23B, and 23C).

In this manner, at the same time as communication of the suction leak hole 68 with the exterior is shut off, the piston body 45 is pushed into the cylinder 43 by the operation button 74, as illustrated in FIG. 23B and FIG. 23C, and the valve body 77 penetrates to below the valve seat 76. The valve part constituted by the valve seat 76 and valve body 77 accordingly opens, and the inside of the cylinder 43 and inside of the attachment tube 41 communicate with each other. The guide part 78 is provided so as to bridge lower and upper parts of the valve seat 76, and therefore makes the insides of the cylinder 43 and attachment tube 41 communicate with each other. Accordingly, the insides of the cylinder 43 and attachment tube 41 communicate with each other, shut off from the exterior. Therefore, the metal suction mouthpiece 35 can suction, for example, liquid in a body cavity from the channel opening 26 through the insertion channel 25 and channel 28, in a direction denoted by arrows in FIGS. 23B and 23C. During this suction, the flap 162 of the suction tube connection part 57 opens and releases the suction channel.

Since the operation button 74 is pressed during suction, the valve body part 105 is pressed into contact with the second divisional air-feed channel 82, thereby shutting off the second divisional air-feed channel 82. In this manner, the first divisional air-feed channel 81 and the second divisional air-feed channel 82 are surely separated from each other. As a result of this, air-feed is not performed even if the air-feed leak hole 85 is closed by mistake. Further, even if a suctioned material enters the second divisional air-feed channel 82, the suctioned material is prevented from taking into the side of the first divisional air-feed channel 81, and prevented from entering into the metal air-feed mouthpiece 36, from being emitted through the air-feed leak hole 85, and from entering into the metal air-feed mouthpiece 36.

Thus, in the present embodiment, when the metal suction mouthpiece 35 is connected to the air-feed tube 39 by mistake, the suction channel is closed by the valve body part 105, and air-feed through the suction channel is prevented.

Also in the present embodiment, when the metal air-feed mouthpiece 36 is connected to the suction tube 38 by mistake, an external gas is suctioned from the air-feed leak hole 85. Therefore, suction to a depth beyond the first divisional air-feed channel 81 is prevented. Further, when the air-feed leak hole 85 is closed by mistake, a pressure in the side of the first divisional air-feed channel 81 decreases, and the pressure in the second communication channel 88 decreases accordingly. As a result, the valve body 99 is pulled by the valve seat 96, thereby preventing the inside of the operation button 74 from being suctioned.

When the fluid control apparatus 30 is constituted by a disposable product, the fluid control apparatus 30 is detached from the attachment tube 41 after use of the endoscope 10. Only the endoscope 10 is subjected to cleaning. Accordingly, the insertion channel 25 can be easily cleaned.

Meanwhile, in the fluid control apparatus 30 according to the present embodiment, the air-feed tube 39 is connected to the piston body 45. The piston body 45 protrudes out of the cylinder 43, and the air-feed tube 39 is drawn out to near the top end of the piston body 45. Therefore, a load applied to the piston body 45 is large, for example, due to flapping of the air-feed tube 39. Further, when the endoscope 10 and the air-feed tube 39 move abruptly, the piston body 45 is applied with an impactive load. Thus, if the piston body 45 is applied with various loads, a posture of the endoscope 10 is influenced. Further, as the piston body 45 rotates about an axis thereof, torque is applied through the piston body 45 to the cylinder 43. In this manner, there is a case in which the torque exceeds an engagement force for the attachment tube 41 due to a function of the release cam, and there is a risk that the cylinder 43 unintentionally falls out of the attachment tube 41. Further, when the piston body 45 rotates about the axis thereof due to a load received from the air-feed tube 39, a position of the air-feed leak hole 85 shifts from a predetermined operation position, and there is a risk that an operation of closing the hole with an operator's finger is hindered.

However, in the present embodiment, the top end of the elastic member 60 is fixedly connected to the top end of the piston body 45. Therefore, when the piston body 45 rotates about the axis thereof due to the load of the air-feed tube 39, the top end of the elastic member 60 rotates together and is elastically twisted. Accordingly, the load applied to the piston body 45 is absorbed and reduced by flapping of the air-feed tube 39, even if an operator or an assistant moves the air-feed tube 39 or the endoscope 10 in the course of manually operating the endoscope. In particular, even if the endoscope 10 or the air-feed tube 39 is abruptly moved, an impactive load thereof is absorbed and reduced. Therefore, adverse influence on the posture of the endoscope 10 decreases.

Further, when the cylinder 43 rotates and is detached from the endoscope 10, the torque applied to the piston body 45 is applied to the side of the cylinder 43 through the piston body 45. Then, the torque exceeds the engagement force of the cylinder 43 engaging with the attachment tube 41 due to a function of the release cam. Further, there is a risk that the cylinder 43 unintentionally falls out of the attachment tube 41. However, in the present embodiment, the elastic member 60 relaxes the torque applied to the piston body 45. Accordingly, the cylinder 43 does not fall out of the attachment tube 41 with which the cylinder 43 is engaged, and the cylinder 43 does not unintentionally fall out of the attachment tube 41. When the load applied to the piston body 45 is decreased by the piston body 45, twisting of the elastic member 60 about the axis thereof is released, and the elastic member 60 returns to an original position. Accordingly, a position of the suction leak hole 68 returns to an original position.

Although a preferred embodiment and modifications of the present invention have been described above, the present invention is not limited to the above embodiment and modifications described above. Further, the embodiment and modifications can be variously combined with each other. Further, the above embodiment has described fluid transfer in air-feed and suction. However, the embodiment may be applied to air-feed, suction, and fluid transfer such as liquid-feed.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:
1. An endoscopic fluid control apparatus comprising:
a cylinder which is attachable to an attachment part attached to an endoscope, and includes a first channel which transfers fluid to an insertion channel of the endoscope;
a piston which is set on the cylinder and includes:
a valve part configured to be moved relative to the cylinder between a first position where the first channel is open relative to the insertion channel and a second position where the first channel is closed relative to the insertion channel,
a connection port part for connecting a fluid tube configured to transfer fluid, and
a second channel which transfers the fluid from the connection port part to the insertion channel;
an elastic member which holds the piston to be movable relative to the cylinder between the second position and the first position;
a first engagement part which engages the piston and the elastic member with each other so as not to rotate about an axis of movement of the piston; and
a second engagement part which engages the cylinder and the elastic member with each other so as not to rotate about an axis of movement of the cylinder;
the elastic member having leak holes positioned and configured to communicate with an outside and the first channel through an inside of the elastic member, and the leak holes are substantially closed by folding the elastic member;
the connection port part being positioned perpendicular to a longitudinal axis of the piston and protruding from an upper end part of the piston;
the first engagement part being positioned on the piston and engaging with an upper end part of the elastic member; and the second engagement part being positioned on an upper end part of the cylinder and engaging with a lower end part of the elastic member; and a valve member which is provided on the piston and shuts off the second channel, wherein the first engagement part is formed by connecting the valve member and the elastic member to each other.

2. The endoscopic fluid control apparatus of claim 1, wherein the valve member and the elastic member are formed to be integral with each other.

3. The endoscopic fluid control apparatus of claim 2, wherein the elastic member is configured in a structure in which a part of the second engagement part to be engaged on the cylinder continues over a whole circumference thereof.

4. The endoscopic fluid control apparatus of claim 1, wherein the second engagement part includes a cover which covers a part engaging the cylinder and the elastic member with each other.

* * * * *